(12) United States Patent
Nariyuki et al.

(10) Patent No.: US 10,219,962 B2
(45) Date of Patent: Mar. 5, 2019

(54) INCUBATOR HOOD, INCUBATOR HAVING THE SAME, HYDROPHILIC SHEET FOR INCUBATORS, AND HYDROPHILIC ANTIBACTERIAL FILM FOR INCUBATORS

(71) Applicant: FUJIFILM Corporation, Tokyo (JP)

(72) Inventors: Fumito Nariyuki, Ashigara-kami-gun (JP); Toshiyuki Nabeta, Ashigara-kami-gun (JP); Michihiro Shibata, Ashigara-kami-gun (JP); Hideo Nagasaki, Ashigara-kami-gun (JP); Setsuko Shiratsuchi, Ashigara-kami-gun (JP); Shigeaki Ohtani, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 728 days.

(21) Appl. No.: 14/811,506

(22) Filed: Jul. 28, 2015

(65) Prior Publication Data

US 2016/0030616 A1    Feb. 4, 2016

(30) Foreign Application Priority Data

Jul. 29, 2014  (JP) .................................. 2014-154206
Jul. 21, 2015  (JP) .................................. 2015-143631

(51) Int. Cl.
   *A61G 11/00*    (2006.01)
   *A01N 25/34*    (2006.01)
(52) U.S. Cl.
   CPC .............. *A61G 11/00* (2013.01); *A01N 25/34* (2013.01)
(58) Field of Classification Search
   None
   See application file for complete search history.

(56) References Cited

U.S. PATENT DOCUMENTS

2005/0065231 A1*  3/2005  Sasaki .................... A01N 59/16
                                                    523/122
2005/0203237 A1*  9/2005  Cornelius Maria Dekkers ..........
                                                    A01N 59/16
                                                    524/450

(Continued)

FOREIGN PATENT DOCUMENTS

JP         9-131389 A     5/1997
JP      2002-113053 A     4/2002

(Continued)

OTHER PUBLICATIONS

Japanese Office Action and English translation thereof, dated Oct. 25, 2016, for corresponding Japanese Application No. 2015-143631.

(Continued)

*Primary Examiner* — Thaddeus B Cox
(74) *Attorney, Agent, or Firm* — Birch, Stewart, Kolasch & Birch, LLP

(57) ABSTRACT

The present invention provides an incubator hood having a hydrophilized portion on at least a part of its inner surface, the hydrophilized portion containing a hydrophilic polymer and an antibacterial agent, and a surface of the hydrophilized portion having a water contact angle of up to 30°, and also provides an incubator having the incubator hood as well as a hydrophilic sheet and a hydrophilic antibacterial film for use in forming the hydrophilized portion on the incubator hood. Thus the present invention provides an incubator hood, an incubator, a hydrophilic sheet and a hydrophilic antibacterial film that have excellent antifogging properties and antibacterial properties and can suppress the growth of bacteria.

11 Claims, 5 Drawing Sheets

(56) References Cited

U.S. PATENT DOCUMENTS

| | | | | |
|---|---|---|---|---|
| 2009/0291500 A1* | 11/2009 | Takada | ............. | C08F 2/18 |
| | | | | 435/396 |
| 2012/0034435 A1* | 2/2012 | Borrelli | ............. | C03C 17/30 |
| | | | | 428/210 |
| 2012/0215054 A1 | 8/2012 | Rodrigues | | |
| 2012/0261054 A1* | 10/2012 | Blucher | ............. | A01N 25/34 |
| | | | | 156/85 |
| 2014/0135569 A1* | 5/2014 | Hansmann | ............. | A61G 11/00 |
| | | | | 600/22 |

FOREIGN PATENT DOCUMENTS

| | | |
|---|---|---|
| JP | 2002-337277 A | 11/2002 |
| JP | 2009-73923 A | 4/2009 |
| JP | 2010-36368 A | 2/2010 |
| JP | 2010-83141 A | 4/2010 |

OTHER PUBLICATIONS

Chinese Office Action and English translation thereof, dated Jul. 4, 2018, for corresponding Chinese Application No. 201510455813.4.

\* cited by examiner

INCUBATOR HOOD, INCUBATOR HAVING THE SAME, HYDROPHILIC SHEET FOR INCUBATORS, AND HYDROPHILIC ANTIBACTERIAL FILM FOR INCUBATORS

CROSS-REFERENCE TO RELATED APPLICATIONS

The present application claims priority under 35 U.S.C. § 119 to Japanese Patent Application No. 2014-154206 filed on Jul. 29, 2014 and Japanese Patent Application No. 2015-143631 filed on Jul. 21, 2015. Each of the above applications is hereby expressly incorporated by reference, in its entirety, into the present application.

BACKGROUND OF THE INVENTION

The present invention relates to an incubator hood, an incubator having the incubator hood, a hydrophilic sheet for incubators, and a hydrophilic antibacterial film for incubators, particularly to an incubator hood that is used for housing a premature neonate, a sickly infant, a neonate after surgery or the like and has a hydrophilized portion on at least a part of its inner surface, an incubator having the incubator hood, a hydrophilic sheet for incubators for use in forming the incubator hood, and a hydrophilic antibacterial film for incubators.

Conventionally, incubators have been used for providing premature neonates who have low adaptability to an environment outside of wombs of their mothers, sickly infants, neonates after surgery and the like (hereinafter represented by "neonate(s)") with the environment allowing them to grow during a certain period of time in infancy by means of heat retention, humidity retention, isolation and observation or monitoring.

Such an incubator has the configuration that enables a neonate to be isolated from the outside, enables the internal temperature, humidity and the like to be automatically adjusted and also enables the internal oxygen concentration to be freely adjusted in order to provide a proper environment to the neonate having low adaptability to an environment. The upper portion of the incubator is constituted by an incubator hood that is composed of transparent synthetic resin and that covers a base table serving as a bed on which a neonate lies, and the thus configured incubator hood makes the observation easy. The incubator hood has two or four arm holes at its lateral and/or front side or in addition thereto, two arm holes at its back side to allow two hands to enter the incubator through two of the arm holes to give various treatments such as suckling, care and medical examination to the neonate and thus, the infection prevention effect is also taken into account.

Four important functions of such incubators are heat retention, humidification, infection prevention and oxygenation.

The heat retention function is the most important function for incubators. Neonates have a larger body surface area per unit weight and a smaller subcutaneous tissue thickness compared to adults and therefore, have great difficulty in maintaining their body temperatures by themselves. When much energy is used to maintain the body temperature, this results in shortage of energy to be used in growth. Therefore, it is necessary to always maintain the temperature at which a neonate is allowed to have a constant body temperature with the minimum energy consumption.

The humidification function is required because the humidity in an incubator needs to be controlled in order to prevent water evaporation from a neonate's body and succeeding heat loss of the neonate. In particular, in the case of extremely premature neonates and minimum immature neonates, a high humidity of 80% to 90% need to be maintained over one week immediately after birth.

The infection prevention function is required because it is "infection" that babies having low resistance need to be careful about. Since the environment (temperature and humidity) comfortable for neonates is also a good environment for bacteria and viruses to reproduce, when bacteria and viruses (hereinafter represented by "bacteria") and the like are present in the air entering an incubator, the bacteria and the like easily reproduce and may cause the infection. Therefore, the air to enter an incubator needs to be filtered by a filter or the like to thereby prevent the entry of dust, bacteria and the like.

The oxygenation function is required because it is necessary to send oxygen indispensable for a neonate. Neonates born with the lungs not yet fully developed need an oxygen concentration higher than usual.

As described above, the interior of an incubator is usually kept at a temperature higher than room temperature and a high humidity for controlling the neonate's body temperature. Consequently, the inner surface of a transparent incubator hood fogs up or has condensation, which impairs the visibility of the interior of the incubator. As a result, this may hamper the observation of neonate's condition as well as suckling, care, medical examination and other various treatments for the neonate. Meanwhile, dust, bacteria and the like are removed by a filter or the like from the air entering the incubator and hence, bacteria and the like would not reproduce in the normal environment in the incubator even when the inner surface of the incubator hood fogs up to some extent. If, however, the condensation occurs on the inner surface and stays for a long period of time, various bacteria and mold may grow at the portion having the condensation and infect the neonate.

Thus, when the inner surface of the incubator hood fogs up or has condensation, the fog and the condensation need to be wiped off but wiping with the neonate lying in the incubator is dangerous and also it is dangerous to transfer the neonate to another incubator for avoiding an antiseptic solution or the like used in wiping because the environment greatly changes.

To cope with it, one possible measure is to apply an antifogging agent or an antibacterial agent onto the inner surface of the incubator hood. However, such an antifogging agent or antibacterial agent may be dissolved and released in the high humidity environment in the incubator, so that the effects thereof decrease and in addition, the risk that the released antifogging agent or antibacterial agent may affect the neonate cannot be ignored.

JP 2002-113053 A discloses the technique in which at least a part of the inner surface of a plastic hood, i.e., an incubator hood made of plastic is coated with a photocatalyst so as to have antifogging properties and antibacterial properties whereby the condensation on the inner surface of the plastic hood and the growth of mold and various bacteria can be prevented and a neonate can safely receive care during the stay in the incubator.

When it comes to antibacterial properties, medical devices used in the medical settings continuously come in contact with an unspecified large number of people such as patients and medical personnel and therefore, in recent years, the technique in which an antibacterial layer is provided on a surface of each device to suppress the growth of bacteria and reduce the risk of infection causing diseases has been drawing attention as disclosed by, for example, JP 09-131389 A and JP 2002-337277 A.

JP 09-131389 A discloses a silver antibacterial agent in which a silica gel carrier carries a silver complex and a controlled release antibacterial material composed of a silica gel and an organic binder.

JP 2002-337277 A discloses a front panel made up of a scratch-resistant film including an antibacterial agent composed of a silver-containing phosphate double salt and a substrate.

SUMMARY OF THE INVENTION

Meanwhile, in certain cases, incubators were conventionally placed under a lighting environment all day in order to handle emergency but nowadays, the outer surface of each incubator hood is covered by a light control cover (shade cover) or the like in a Neonatal Intensive Care Unit (NICU) to thereby reduce stress caused by light and sound.

While JP 2002-113053 A describes that the photocatalyst exhibits antifogging properties as well as antibacterial properties, light irradiation is essential for achieving antibacterial properties and antifogging properties such as condensation prevention and therefore, the photocatalyst is unfavorable for an incubator hood having the outer surface covered with a light control cover (shade cover) or the like and thus used under a light shielding environment.

The present invention has been made to solve the problems of the prior art described above and aims at providing an incubator hood that can prevent or suppress the occurrence of fog or condensation on its inner surface and prevent or suppress the growth of bacteria, namely, that has excellent antifogging properties and antibacterial properties, an incubator having the incubator hood, a hydrophilic sheet for incubators for use in forming the incubator hood, and a hydrophilic antibacterial film for incubators.

In order to attain the objects above, the present invention provides as its first aspect an incubator hood having a hydrophilized portion on at least a part of its inner surface, wherein the hydrophilized portion contains a hydrophilic polymer and an antibacterial agent, and wherein a surface of the hydrophilized portion has a water contact angle of up to 30°.

In addition, in order to attain the objects above, the present invention provides as its second aspect a hydrophilic sheet for incubators attached to at least a part of an inner surface of an incubator hood of an incubator having a base table on which a neonate lies and the incubator hood which covers the neonate lying on the base table to form inside an accommodating room of the neonate, comprising: a hydrophilized portion provided on at least a part of an outer surface of the hydrophilic sheet, wherein the hydrophilized portion contains a hydrophilic polymer and an antibacterial agent, and wherein a surface of the hydrophilized portion has a water contact angle of up to 30°.

In addition, in order to attain the objects above, the present invention provides as its third aspect a hydrophilic antibacterial film for incubators formed on at least a part of an inner surface of an incubator hood of an incubator having a base table on which a neonate lies and the incubator hood which covers the neonate lying on the base table to form inside an accommodating room of the neonate, in order to form a hydrophilized portion on at least a part of the inner surface of the incubator hood, at least a part of the hydrophilic antibacterial film being hydrophilic, wherein the hydrophilized portion exhibiting hydrophilicity contains a hydrophilic polymer and an antibacterial agent, and wherein a surface of the hydrophilized portion has a water contact angle of up to 30°.

In the first, second and third aspects, the antibacterial agent may be composed of at least one type of silver-containing antibacterial agent, and the incubator hood may satisfy relations expressed by formulae (1) and (2) below when a silver content per unit area in the hydrophilized portion is represented by P and an amount of silver ions per unit area as measured by an extraction test is represented by Q, $$6.0 \leq P/Q \qquad \text{Formula (1)}$$

$$15.0 \leq Q \qquad \text{Formula (2)}$$

where a unit of P is $ng/cm^2$ and a unit of Q is $ng/cm^2$, the extraction test being a test for determining the amount of silver ions per unit area represented by Q by using 1/500 nutrient broth defined in JIS Z 2801:2010 as extraction liquid, controlling the extraction liquid to a temperature of 35±1° C., holding the hydrophilized portion in contact with the extraction liquid for 1 hour, measuring an amount of silver ions extracted in the extraction liquid and dividing the amount of silver ions obtained by a contact area of the hydrophilized portion with the extraction liquid.

It is preferable to satisfy a relation expressed by formula (3):

$$15.0 \leq Q \leq 25.0. \qquad \text{Formula (3)}$$

Preferably, the antibacterial agent is composed of a first antibacterial agent containing silver and a second antibacterial agent containing silver and different from the first antibacterial agent.

Preferably, the first antibacterial agent contains silver and a carrier selected from the group consisting of calcium zinc phosphate and calcium phosphate, and the second antibacterial agent contains silver and a carrier composed of zeolite.

In the first, second and third aspects, the antibacterial agent may be composed of at least one type of silver-containing antibacterial agent, and an amount of silver ions per unit area as measured by an extraction test may be 15 to 50 $ng/cm^2$, the extraction test being a test for determining the amount of silver ions per unit area by using 1/500 nutrient broth defined in JIS Z 2801:2010 as extraction liquid, controlling the extraction liquid to a temperature of 35±1° C., holding the hydrophilized portion in contact with the extraction liquid for 1 hour, measuring an amount of silver ions extracted in the extraction liquid and dividing the amount of silver ions obtained by a contact area of the hydrophilized portion with the extraction liquid, a unit of the amount of silver ions being ng, a unit of the contact area being $cm^2$, and a unit of the amount of silver ions per unit area being $ng/cm^2$.

Preferably, the antibacterial agent is a silver-carrying carrier including a carrier and silver carried on the carrier.

In the first, second and third aspects, the hydrophilized portion may further contain a porous carrier that is capable of adsorbing silver ions and may carry silver; the antibacterial agent may contain silver; and the incubator hood may satisfy relations expressed by formulae (4) and (5) below when an average particle size of the antibacterial agent is Da, an average particle size of the porous carrier is Db and an average thickness of the hydrophilized portion is T, $$T/Da > 3.0 \qquad \text{Formula (4)}$$

$$T/Db \leq 3.0 \qquad \text{Formula (5)}$$

where units of Da, Db and T are μm.

Preferably, silver is carried on the porous carrier.

Preferably, the average particle sizes represented by Da and Db satisfy a relation expressed by formula (6):

$$Db/Da \leq 3.5. \qquad \text{Formula (6)}$$

Preferably, the porous carrier is contained at a content of up to 0.5 wt % with respect to a total weight of the hydrophilized portion.

Preferably, the antibacterial agent contains silver and a carrier selected from the group consisting of calcium zinc phosphate and calcium phosphate, and the porous carrier contains silver and a carrier composed of zeolite.

In the first, second and third aspects, preferably, the surface of the hydrophilized portion has a surface roughness Ra of 2 to 15 μm.

Preferably, the hydrophilized portion has an average thickness of 1 to 10 μm.

Preferably, the antibacterial agent is contained at a content of 0.001 to 5 wt % with respect to a total weight of the hydrophilized portion.

Preferably, the antibacterial agent contains at least one selected from the group consisting of silver-carrying ceramic particles and silver particles.

In order to attain the objects above, the present invention provides as its fourth aspect an incubator, comprising: the incubator hood in the first aspect; and a base table on which a neonate lies, wherein the incubator hood covers the neonate lying on the base table to form inside an accommodating room of the neonate, and wherein the hydrophilized portion is provided on, of the inner surface of the incubator hood, at least a part of the inner surface corresponding to an observation portion that allows observation of the neonate accommodated in the accommodating room from outside of the accommodating room.

Preferably, the hydrophilized portion is provided on the inner surface of a front part and/or an upper part of the incubator hood.

Preferably, the hydrophilized portion is provided on the inner surface of side parts and/or a back part of the incubator hood.

Preferably, the hydrophilized portion is provided on the inner surface of an upper part of the incubator hood.

Preferably, the hydrophilized portion is provided over an entire area of the inner surface of the incubator hood.

According to the present invention, since the incubator hood is provided on its inner surface with the hydrophilized portion, the inner surface of the transparent incubator hood less readily fogs up and owing to antibacterial properties, bacteria and the like are unlikely to be attached to the incubator hood even when hands enter the incubator to work through the arm holes at the incubator hood.

In other words, the present invention provides the incubator hood excellent in antifogging properties and antibacterial properties that can prevent or suppress the occurrence of fog on its inner surface and prevent or suppress the growth of bacteria, the incubator having the incubator hood, the hydrophilic sheet for incubators for use in forming the incubator hood, and the hydrophilic antibacterial film for incubators.

DETAILED DESCRIPTION OF THE INVENTION

An incubator hood, an incubator having the incubator hood, a hydrophilic sheet for incubators and a hydrophilic antibacterial film for incubators will be described in detail based on preferred embodiments shown in the appended drawings.

Note that value ranges expressed with "to" in this specification each refer to a range including the upper limit and the lower limit before and after "to."

Embodiment 1

Figure 1:
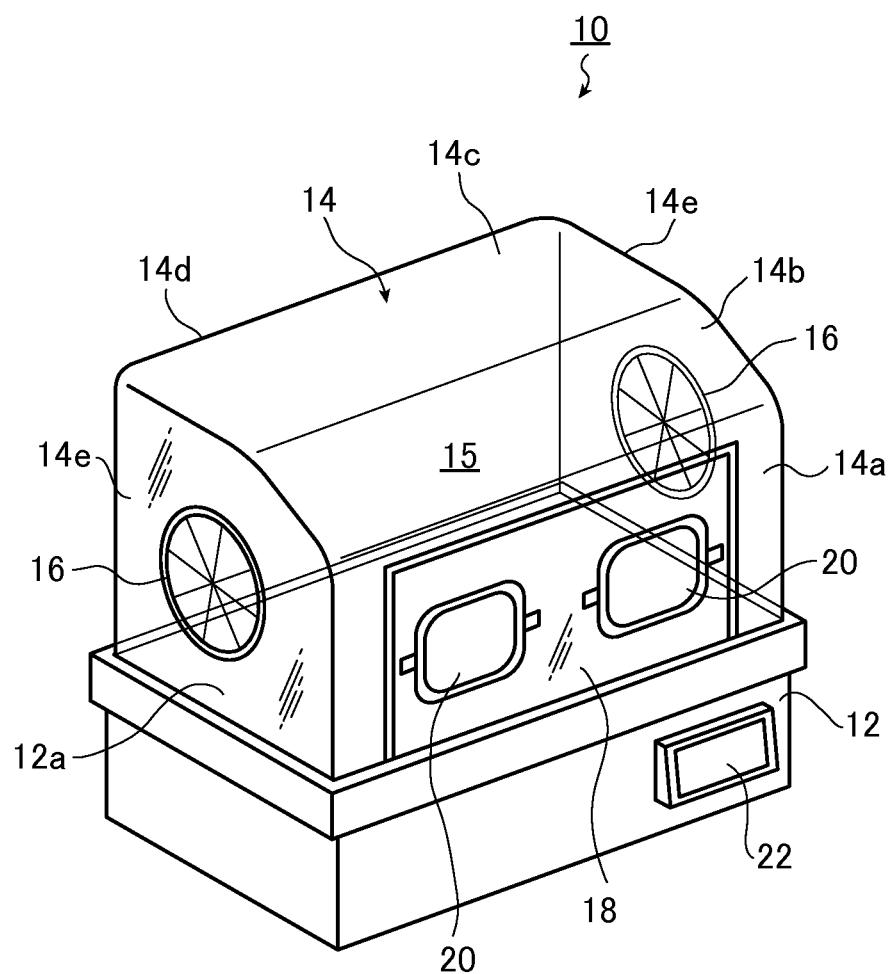
FIG. 1 is a perspective view showing an example of an incubator according to Embodiment 1 of the invention.

FIG. 1 is a perspective view showing an example of an incubator according to Embodiment 1 of the invention.

An incubator 10 shown in FIG. 1 includes a base table 12 serving as a bed on which a premature neonate who has low adaptability to an environment outside of the womb of his/her mother, a sickly infant or a neonate after surgery (hereinafter represented by "neonate") lies and an incubator hood 14 covering at least a part of the base table 12 to thereby form an accommodating room for accommodating a neonate therein.

The base table 12 takes on a cuboid shape having a rectangular flat upper surface 12a on which a mat, a cotton blanket, a towel or the like is spread out to thereby constitute a bed on which a neonate lies.

The incubator hood 14 used to cover a neonate lying on the base table 12 is composed of a transparent plastic housing having a substantially pentagonal prism shape in which one edge is cut off to form an inclined part and includes, from the front side, a front part 14a, an inclined part 14b, an upper part 14c and a back part 14d as well as a pair of pentagonal side parts 14e covering opposite lateral sides each surrounded by the above parts. A rectangular bottom part surrounded by the front part 14a, the back part 14d and the pair of side parts 14e is open. The front part 14a and the inclined part 14b are also called "front surface part."

The incubator hood 14 is detachably attached to the upper portion of the upper surface 12a of the base table 12 so as to cover the space above the upper surface 12a and forms, together with the base table 12, an accommodating room 15 isolated from the outside for use in accommodating a neonate therein.

A surface to face an observer or a caregiver such as a medical professional during observation or treatment of a neonate is called "front surface part" and a surface located at the upper side in the vertical direction in the state where a neonate is accommodated inside is called "upper surface part." A surface facing the front surface part is called "back surface part" and two surfaces each surrounded by the front surface part, the back surface part and the upper surface part are called "side surface parts."

While in the illustrated example, the front surface part is constituted by the front part 14*a* and the inclined part 14*b*, the present invention is not limited thereto. The inclined part 14*b* may be replaced by a curved part connecting the upper edge of the front part 14*a* and the front edge of the upper part 14*c*; a curved part may be provided at least either between the front part 14*a* and the inclined part 14*b* or between the inclined part 14*b* and the upper part 14*c*; or the upper edge of the front part 14*a* and the front edge of the upper part 14*c* may be extended to directly join without having the inclined part 14*b* or a curved part so that the incubator hood 14 has a cuboid shape.

In addition, an inclined part and/or a curved part may be provided at least one of the positions between the front part 14*a* and each side part 14*e*, between the upper part 14*c* and the back part 14*d*, between the upper part 14*c* and each side part 14*e* and between the back part 14*d* and each side part 14*e*, and either or both edges of each inclined part thus provided may be constituted by curved parts.

The pair of side parts 14*e* of the incubator hood 14 separately have arm holes 16 that allow a medical professional such as a physician or a nurse to insert his/her hands into the incubator 10 to give various treatments such as suckling, care and medical examination to a neonate.

The front part 14*a* of the incubator hood 14 has an openable and closable front door 18. By opening the front door 18, a neonate can be brought into the accommodating room 15 of the incubator 10 to be accommodated and taken out of the accommodating room 15.

As illustrated, a pair of openable and closable arm holes 20 may be provided at the front door 18 to allow a medical professional to insert his/her hands into the incubator 10 to give various treatments such as suckling, care and medical examination to a neonate.

While in the illustrated example, the pair of arm holes 16 are separately provided at the pair of side parts 14*e* and the pair of arm holes 20 are provided at the front door 18 of the front part 14*a*, the present invention is not limited thereto and there may be provided only either of the pairs of arm holes 16 and 20 and alternatively, instead of or in addition to the pairs of arm holes 16 and 20, another pair of arm holes (not illustrated) may be provided at the back surface part.

Needless to say, the incubator 10 of the invention has the above-described four important functions of heat retention, humidification, infection prevention and oxygenation and although not illustrated, includes heat retention means, humidification means, infection prevention means and oxygenation means for those functions. Known means can be employed for the heat retention means, the humidification means, the infection prevention means and the oxygenation means and therefore, the explanation thereof will not be made.

A control panel 22 of touch panel type is provided on the front side of the base table 12 of the incubator 10 to allow appropriate control of the heat retention means, the humidification means, the infection prevention means and the oxygenation means.

The heat retention means, the humidification means, the infection prevention means and the oxygenation means are appropriately controlled using the control panel 22 whereby the incubator 10 can have the internal environment in which the temperature, the humidity and the oxygen concentration are properly maintained and the air environment in which neither bacteria nor mold occurs, no dust is present and no infection is caused.

The incubator 10 of the invention is configured as described above. In this configuration, a hydrophilized portion is provided on at least a part of the inner surface of the incubator hood 14, for instance, a part of the inner surface corresponding to an observation portion through which a neonate accommodated in the accommodating room 15 of the incubator 10 is observed. The term "inner surface" refers to a surface on the side facing the space accommodating a neonate.

In the present invention, the hydrophilized portion is preferably disposed on at least a part of the inner surface of the incubator hood 14, for instance, a part of the inner surface corresponding to the observation portion that allows the observation from the outside. More specifically, the hydrophilized portion is preferably provided on the inner surface of the front surface part, for example, the inner surface of the front door 18 of the front part 14*a*, the entire front part 14*a*, the inclined part 14*b* or the front and inclined parts 14*a* and 14*b*. In particular, the hydrophilized portion is more preferably provided on the inner surface of the front and inclined parts 14*a* and 14*b*.

In addition, it is preferred to provide the hydrophilized portion on the inner surface of the upper portion, i.e., the upper and inclined parts 14*c* and 14*b* of the incubator hood for the following reason.

Figure 2:
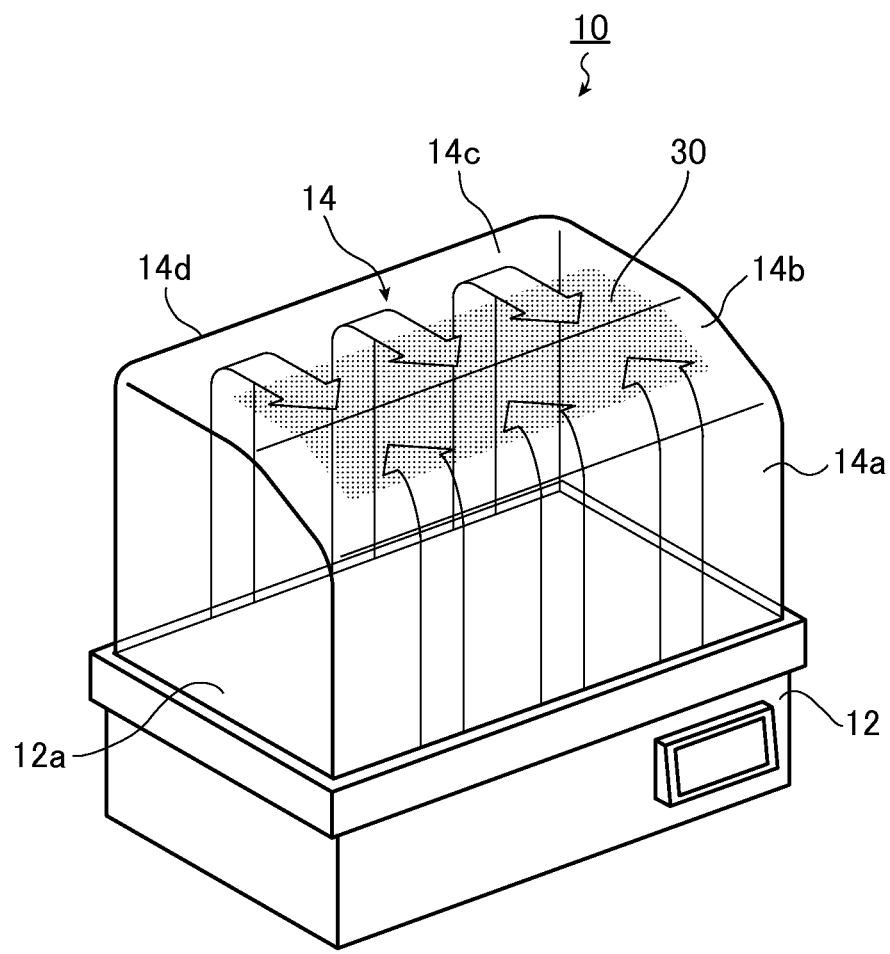
FIG. 2 is a view for explaining the air circulation in an incubator.

FIG. 2 is a view showing the air circulation in an incubator. The incubator shown in FIG. 2 is the same as the incubator 10 shown in FIG. 1 although some members are omitted.

In a general incubator, the air prepared by removing dust and bacteria from the outside air and adjusting the temperature, the humidity and the oxygen concentration to predetermined values is gently sent from the bottom at the inner side of the front part 14*a* and the back part 14*d* of the incubator hood toward the upper part 14*c* and the inclined part 14*b*, thereby maintaining the temperature in the incubator.

When the inner surface of the incubator hood has condensation, however, the air flowing from the front part 14*a* side of the incubator hood and the air flowing from the back part 14*d* side thereof collide at a ceiling portion of the incubator and this may cause water droplets attached to the incubator hood to fall on a lying neonate. Such water droplets falling on a neonate may decrease the neonate's body temperature or cause viral or bacterial infection of the neonate.

Therefore, it is preferred to provide the hydrophilized portion on the inner surface of the incubator hood at the position from which generated water droplets are likely to fall to a neonate due to the flow of air circulating in the incubator hood. In other words, the provision of the hydrophilized portion at the upper portion (upper part 14*c* and inclined part 14*b*) of the incubator hood, preferably at a position 30 facing a neonate lying on the upper surface 12*a* of the incubator 10 can prevent water droplets from falling to a neonate.

In the present invention, the position where the hydrophilized portion is provided is not limited to the front surface part or the upper portion (upper part 14c and inclined part 14b) of the incubator hood 14 and the hydrophilized portion may be provided on the inner surface of, instead of or in addition to the front surface part or the upper portion, the back part 14d and/or the pair of side parts 14e or the entire inner surface of the incubator hood 14.

Moreover, the hydrophilized portion of the invention has, in addition to superhydrophilicity, high antibacterial properties and therefore, may be provided on the surface of the touch panel of the control panel 22.

The incubator 10 of the invention is basically has the foregoing configuration but is not limited thereto. Any known incubator may be employed as long as the hydrophilized portion of the invention can be provided on the inner surface of the incubator hood 14.

The hydrophilized portion of the invention is provided on at least a part of the inner surface of the incubator hood 14 and serves to uniformly scatter water droplets on a film surface of the hydrophilized portion to thereby form a water film of a uniform thickness in the environment in the incubator hood 14 with a temperature higher than room temperature and a high humidity. As a result, the hydrophilized portion can prevent the occurrence of fog or condensation and maintain excellent visibility of the transparent incubator hood 14. Therefore, it is possible to easily and reliably observe the condition of a neonate in the incubator 10 through the hydrophilized portion of the incubator hood 14, to give various treatments such as suckling, care and medical examination to the neonate with hands inserted from the pair of arm holes 18 or 20 and to prevent or suppress the growth of bacteria, mold or the like so that the neonate can avoid infection.

In addition, the hydrophilized portion of the invention has a small water contact angle and therefore, even when a water droplet is generated on the inner surface of the incubator hood, the water droplet immediately spreads on the hydrophilized portion. Hence, it is possible to prevent water droplets from falling to a neonate and therefore avoid the decrease of the neonate's body temperature or the infection of the neonate.

In addition, since the hydrophilized portion of the invention contains an antibacterial agent and has high antibacterial properties, it is possible to more effectively prevent or suppress the growth of bacteria, mold or the like so that a neonate can more effectively avoid infection.

In addition, since the hydrophilized portion of the invention has high hydrophilicity, the antibacterial agent dispersed in the hydrophilized portion can also be used so as to exert the antibacterial action. Conventionally, when formalin disinfection, which is a general method for disinfecting incubator hoods, is frequently performed, there has been a problem in that the incubator hood cannot retain antibacterial properties and antifogging properties over long periods. However, according to the present invention, even when formalin disinfection is frequently performed on the incubator hood, the incubator hood can constantly retain antibacterial properties and antifogging properties at its surface and thereby have a longer life.

The hydrophilized portion contains at least a hydrophilic polymer and an antibacterial agent.

Materials contained in the hydrophilized portion are described below in detail.

(Hydrophilic Polymer)

The hydrophilic polymer is a polymer having a hydrophilic group.

The type of the hydrophilic group is not particularly limited and examples thereof include polyoxyalkylene groups (e.g., a polyoxyethylene group, a polyoxypropylene group and a polyoxyalkylene group in which an oxyethylene group, an oxypropylene group are bonded by block or random bonding), an amino group, a carboxyl group, an alkali metal salt of a carboxyl group, a hydroxy group, an alkoxy group, an amido group, a carbamoyl group, a sulfonamido group, a sulfamoyl group, a sulfonate group and an alkali metal salt of a sulfonate group.

The structure of the main chain of the hydrophilic polymer is not particularly limited and examples thereof include polyurethane, poly(meth)acrylate ester, polystyrene, polyester, polyamide, polyimide and polyurea.

The poly(meth)acrylate ester is a conceptual term including both polyacrylate ester and polymethacrylate ester.

A preferred embodiment of the hydrophilic polymer is a polymer obtained by polymerizing a monomer having a hydrophilic group described above.

The monomer having a hydrophilic group refers to a compound having the above-described hydrophilic group and a polymerizable group. The hydrophilic group is as defined above.

The number of the hydrophilic groups in the monomer having a hydrophilic group is not particularly limited and is preferably at least two, more preferably two to six and still more preferably two to three because the hydrophilized portion exhibits higher hidrophilicity.

The type of the polymerizable group is not particularly limited and examples thereof include a radical polymerizable group, a cationic polymerizable group and an anionic polymerizable group. Exemplary radical polymerizable groups include a (meth)acryloyl group, an acrylamide group, a vinyl group, a styryl group and an allyl group. Exemplary cationic polymerizable groups include a vinyl ether group, an oxiranyl group and an oxetanyl group. Of these, the (meth)acryloyl group is preferred.

The (meth)acryloyl group is a conceptual term including both an acryloyl group and a methacryloyl group.

The number of the polymerizable groups in the monomer having a hydrophilic group is not particularly limited and is preferably at least two, more preferably two to six and still more preferably two to three because the resultant hydrophilized portion exhibits higher mechanical strength.

A preferred embodiment of the monomer having a hydrophilic group is a compound represented by formula (A) below.

[Chemical Formula 1]

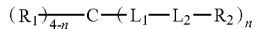

Formula (A)

In formula (A), $R_1$ denotes a substituent. The type of the substituent is not particularly limited and examples thereof include known substituents such as a hydrocarbon group (e.g., an alkyl group, an aryl group) which may have a heteroatom and the above-described hydrophilic group.

$R_2$ denotes a polymerizable group. The polymerizable group is as defined above.

$L_1$ denotes a single bond or a divalent linking group. The type of the divalent linking group is not particularly limited and examples thereof include —O—, —CO—, —NH—, —CO—NH—, —COO—, —O—COO—, an alkylene group, an arylene group, a heteroaryl group and a combination thereof.

L$_2$ denotes a polyoxyalkylene group. The polyoxyalkylene group refers to a group represented by formula (B) below.

$$*-(OR_3)_m-* \quad \text{Formula (B)}$$

In formula (B), R$_3$ denotes an alkylene group (e.g., an ethylene group, a propylene group). m denotes an integer of 2 or more, preferably 2 to 10 and more preferably 2 to 6. * denotes a bonding position.

n denotes an integer of 1 to 4.

The hydrophilic polymer may be obtained by using the above-described monomer having a hydrophilic group and another monomer. In other words, use may be made of a hydrophilic polymer obtained by copolymerizing the monomer having a hydrophilic group and another additional monomer (which is not the monomer having a hydrophilic group).

The type of the additional monomer is not particularly limited and any known monomers having a polymerizable group may be used as appropriate. The polymerizable group is as defined above.

In particular, a multifunctional monomer having two or more polymerizable groups is preferred because the hydrophilized portion exhibits higher mechanical strength. The multifunctional monomer acts as a so-called cross-linking agent.

The number of the polymerizable groups in the multifunctional monomer is not particularly limited and is preferably two to ten and more preferably two to six in terms of higher mechanical strength of the hydrophilized portion and handleability.

Examples of the multifunctional monomer include trimethylol propane triacrylate, tetramethylolmethane tetraacrylate, dipentaerythritol hexaacrylate and pentaerythritol tetraacrylate.

The mixing ratio of the hydrophilic monomer to the additional monomer (in particular, the multifunctional monomer) (weight of hydrophilic monomer/weight of additional monomer) is not particularly limited and is preferably from 0.01 to 10 and more preferably from 0.1 to 10 in terms of ease of control of hydrophilicity of the hydrophilized portion.

The hydrophlized portion preferably contains the above-described hydrophilic polymer as the main ingredient. The term "main ingredient" refers to a hydrophilic polymer content of at least 50 wt %, preferably at least 70 wt % and more preferably at least 90 wt % with respect to the total weight of the hydrophilized portion.

(Antibacterial Agent)

The type of the antibacterial agent contained in the hydrophilized portion is not particularly limited and any known antibacterial agent may be used. Exemplary antibacterial agents include an inorganic antibacterial agent and an organic antibacterial agent (preferably, a water-soluble organic antibacterial agent). As the antibacterial agent, one exerting the bactericidal effect on pathogenic bacteria typified by *Staphylococcus aureus* or *Escherichia coli* is preferably used.

Examples of the organic antibacterial agent include a phenol ether derivative, an imidazole derivative, a sulfone derivative, an N-haloalkylthio compound, an anilide derivative, a pyrrole derivative, a quaternary ammonium salt, a pyridine-based compound, a triazine-based compound, a benzisothiazolin-based compound and an isothiazoline-based compound.

More specific examples thereof include, but are not limited to, 1,2-benzisothiazolin-3-one, N-fluorodichloromethylthio-phthalimide, 2,3,5,6-tetrachloroisophthalonitrile, N-trichloromethylthio-4-cyclohexene-1,2-dicarboximide, 8-copper quinolinate, bis(tributyltin) oxide, 2-(4-thiazolyl) benzimidazole (hereinafter abbreviated as TBZ), methyl 2-benzimidazolecarbamate (hereinafter abbreviated as BCM), 10,10'-oxybisphenoxarsine (hereinafter abbreviated as OBPA), 2,3,5,6-tetrachloro-4-(methylsulfone)pyridine, bis(2-pyridylthio-1-oxide)zinc (hereinafter abbreviated as ZPT), N,N-dimethyl-N'-(fluorodichloromethylthio)-N'-phenylsulfamide<dichlorofluanid>, poly-(hexamethylene biguanide)hydrochloride, dithio-2-2'-bis(benzmethylamide), 2-methyl-4,5-trimethylene-4-isothiazoline-3-one, 2-bromo-2-nitro-1,3-propanediol, hexahydro-1,3-tris-(2-hydroxyethyl)-S-triazine, p-chloro-m-xylenol and 1,2-benzisothiazolin-3-one.

Any of the foregoing organic antibacterial agents can be selected as appropriate in view of hydrophilicity, water resistance, sublimability, safety and the like. Of the foregoing organic antibacterial agents, 2-bromo-2-nitro-1,3-propanediol, TBZ, BCM, OBPA and ZPT are preferred in terms of hydrophilicity, antibacterial effects and costs.

The organic antibacterial agents include natural antibacterial agents. An exemplary natural antibacterial agent is chitosan, which is a basic polysaccharide, obtained by hydrolyzing chitin contained in, for instance, shells of crabs and shrimps.

Examples of the inorganic antibacterial agent include, in the order from high to low bactericidal action, mercury, silver, copper, zinc, iron, lead and bismuth. For example, a carrier carrying metal or metal ion such as silver, copper, zinc, nickel or the like may be used. Examples of the carrier include a silicate-based carrier, a phosphate-based carrier, an oxide (e.g., glass), a potassium titanate and an amino acid.

More specific examples thereof include, but not limited thereto, a zeolite-based antibacterial agent, a calcium silicate-based antibacterial agent, a zirconium phosphate-based antibacterial agent, a calcium phosphate-based antibacterial agent, a zinc oxide-based antibacterial agent, a fusible glass-based antibacterial agent, a silica gel-based antibacterial agent, an activated carbon-based antibacterial agent, a titanium oxide-based antibacterial agent, a titania-based antibacterial agent, an organic metal-based antibacterial agent, an ion exchange ceramic-based antibacterial agent, a layered phosphate-quaternary ammonium salt-based antibacterial agent and an antibacterial stainless steel.

Of the foregoing antibacterial agents, metal particles (particularly preferably copper particles or silver particles), a silver-based inorganic antibacterial agent and an organic antibacterial agent are preferred because of their high antibacterial effects. As the silver-based inorganic antibacterial agent, particularly preferred is ceramic particles carrying silver (silver ceramic particles) and more specifically, use may be made of silver zeolite in which zeolite being a silicate-based carrier carries silver and an antibacterial agent in which silica gel carries silver. As the organic antibacterial agent, 2-bromo-2-nitro-1,3-propanediol, TPN, TBZ, BCM, OBPA and ZPT are preferred.

Commercial silver zeolite-based antibacterial agents particularly preferred include "Zeomic" of Sinanen Co., Ltd., "Silwell" of Fuji Silysia Chemical Ltd. and "Bactenon" of Japan Electronic Materials Corporation. Also preferred are "Novalon" of Toagosei Co., Ltd. in which an inorganic ion exchange ceramic carries silver, "Atomy Ball" of Catalysts & Chemicals Industries Co., Ltd. and "San-ai Bac P" that is a triazine-based antibacterial agent. For the silver particles, "Nanosilver" of Japan-Ion Corporation may be selected. In addition, "Bactekiller" or "Bacteright" of Fuji Chemical Industry Co., Ltd. composed of silver ceramic particles obtained by chemically bonding silver to ceramic may be selected.

In the most preferred embodiment of the antibacterial agent, copper particles, silver particles, copper ceramic particles and silver ceramic particles capable of controlled release of metal ions are preferred, and silver particles and silver ceramic particles are particularly preferred.

The antibacterial agent content in the hydrophilized portion is not particularly limited and is preferably from 0.001 to 15 wt %, more preferably from 0.001 to 10 wt % and even more preferably from 0.001 to 5 wt % with respect to the total weight of the hydrophilized portion in terms of the balance between contaminant removability and antibacterial properties.

When metal particles are used as the antibacterial agent, the antibacterial agent content in the hydrophilized portion is preferably from 0.001 to 10 wt %, more preferably from 0.001 to 5 wt %, even more preferably from 0.001 to 1 wt % and particularly preferably from 0.001 to 0.1 wt % with respect to the total weight of the hydrophilized portion. At an antibacterial agent content of 0.001 wt % or more, the antibacterial effect can be more improved. At an antibacterial agent content of 10 wt % or less, the hydrophilicity does not lowers and the performance does not deteriorate with time, so that there is no adverse effect on antifouling properties.

The metal particles (particularly, silver particles) have an average particle size of preferably 1 nm to 100 nm and more preferably 1 nm to 20 nm. For the metal particles, the smaller the particle size is, the higher the ratio of the surface area to the volume is and antibacterial properties can be exhibited with a smaller amount of the metal particles.

When the silver ceramic particles are used, at a content of 0.1 wt % or more with respect to the total weight of the hydrophilized portion, the antibacterial effect can be more improved. At an antibacterial agent content of 10 wt % or less, the hydrophilicity does not lowers and the performance does not deteriorate with time, so that there is no adverse effect on antifouling properties.

The silver ceramic particles have an average particle size of preferably 0.1 μm to 10 μm and more preferably 0.1 μm to 2 μm.

When the organic antibacterial agent is used as the antibacterial agent, the organic antibacterial agent content is preferably from 1 to 4 wt % with respect to the total weight of the hydrophilized portion in terms of the balance between contaminant removability and antibacterial properties.

In the present invention, the antibacterial agent need not be exposed at a surface of the hydrophilized portion.

Other ingredients than the above-described hydrophilic polymer and the antibacterial agent may be contained in the hydrophilized portion as necessary as long as they do not impair antibacterial properties and antifogging properties.

(Characteristics of Hydrophilized Portion)

The surface of the hydrophilized portion has a water contact angle of up to 30° and because the removability of contaminants on the hydrophilized portion in washing or the like is more excellent, the water contact angle is preferably up to 21° and more preferably up to 15°. The lower limit of the water contact angle is not particularly limited and is often 5° or more due to the characteristics of materials in use.

At a water contact angle in excess of 30°, antibacterial properties and antifogging properties are not sufficiently exhibited and contaminant removability is poor.

In the present specification, the water contact angle is measured by a sessile drop method according to JIS R 3257:1999. The measurement is performed with LSE-ME1 (software: 2win mini) manufactured by NICK Corporation. More specifically, 2 μl of water droplet is dropped on a surface of the hydrophilized portion assuming the level position and the contact angle is measured 20 seconds after the dropping of the water droplet.

The hydrophilized portion surface preferably has fine irregularities. Owing to the fine irregularities, the contact area with an object can be decreased and this results in the reduction of the deposition amount of contaminants derived from sebum and the like. In addition to the decrease of the contact area with contaminants, since gaps tend to be formed between contaminants and the hydrophilized portion surface, water or the like easily enters the gaps and consequently, contaminant removability is improved.

In particular, when the hydrophilized portion has irregularities at a place to come into contact with an object, this leads to the decrease in the contact area with skin of a patient that is an object and mitigates a sticky feeling and a discomfort feeling of the patient during imaging.

The surface roughness Ra at a surface of the hydrophilized portion is not particularly limited and is preferably from 1 μm to 20 μm, more preferably from 2 μm to 15 μm and still more preferably from 3 μm to 6 μm.

The surface roughness Ra is measured as defined in JIS B 0601:2001. Specifically, the surface roughness Ra is determined by measuring the surface roughness at a given five places on the hydrophilized portion surface with a stylus scanning-type profilometer and calculating the average of the measurements. Alternatively, the measurement equivalent to that using the stylus scanning-type profilometer may be performed with a laser microscope having a "roughness measurement mode" (e.g., VK-X200 of Keyence Corporation).

The average thickness of the hydrophilized portion is not particularly limited and is preferably from 0.5 μm to 20 μm and more preferably from 1 μm to 10 μm in terms of contaminant removability and antibacterial properties.

The average thickness of the hydrophilized portion is measured by embedding a sample piece in resin, cutting the resin with a microtome and observing the resultant section with a scanning electron microscope. The thickness is measured at a given ten places in the hydrophilized portion and the arithmetic mean of the measurements is calculated.

(Method of Forming Hydrophilized Portion)

A method of forming the hydrophilized portion is not particularly limited and any known method may be employed. Exemplary methods include a method in which a composition containing the hydrophilic polymer and the antibacterial agent described above is coated to form the hydrophilized portion and a method in which a polymer film containing the hydrophilic polymer and the antibacterial agent and having been separately manufactured is attached to a specified position.

In particular, preferred is a method in which a hydrophilized portion-forming composition containing the monomer having a hydrophilic group and the antibacterial agent described above (hereinafter also simply called "composition") is coated at a specified position to form a coating and the coating is cured to thereby form the hydrophilized portion (coating method) in terms of ease of adjustment of the thickness and the surface profile of the hydrophilized portion.

The composition contains the monomer having a hydrophilic group and the antibacterial agent described above and may additionally contain other ingredients (additional monomer described above, solvent (water or organic solvent)).

The composition may contain a polymerization initiator. The polymerization initiator contained allows the polymerization to efficiently proceed in a coating, thereby forming the hydrophilized portion having excellent mechanical strength. The type of the polymerization initiator is not particularly limited and a suitable type is selected according to a curing method. For instance, a thermal polymerization initiator or a photopolymerization initiator is selected. More specific examples of the polymerization initiators include aromatic ketones such as benzophenone and phenylphosphine oxide, α-hydroxyalkylphenone-based compounds (IRGACURE 184, 127, 2959, DAROCUR 1174 and the like of BASF) and phenylphosphine oxide-based compounds (MAPO: LUCIRIN TPO of BASF, BAPO: IRGACURE 819 of BASF).

The polymerization initiator content in the composition is not particularly limited and is preferably from 0.1 to 15 parts by weight and more preferably from 1 to 6 parts by weight with respect to 100 parts by weight of the total weight of the monomer having a hydrophilic group and the additional monomer.

A method of coating the composition is not particularly limited and any know coating method may be employed.

A curing method is not particularly limited and examples thereof include heating treatment and photoirradiation treatment.

The incubator 10 according to this embodiment basically has the foregoing configuration. The explanation will be made on a method of forming the hydrophilized portion provided on at least a part of, i.e., a specified portion of the inner surface of the incubator hood 14, for instance, a part of the inner surface corresponding to the observation portion that allows the observation from the outside, more specifically, the inner surface of the front surface part including the front part 14a and/or the inclined part 14b, and/or that of the inclined part 14b and the like, and in addition that of the back part 14d and/or the pair of side parts 14e.

The incubator 10 according to this embodiment has the configuration in which the hydrophilized portion is provided at a specified portion of the inner surface of the incubator hood 14. A method of providing the hydrophilized portion at a specified portion of the inner surface of the incubator hood 14 is not particularly limited and any method may be employed. For instance, a hydrophilic sheet having the hydrophilized portion on at least a part of its surface, i.e., on its entire surface or a part of its surface, may be attached to a specified portion of the inner surface of the incubator hood 14 to thereby provide the hydrophilized portion and alternatively, a hydrophilic antibacterial film having a hydrophilic portion on at least a part of its surface, i.e., on its entire surface or a part of its surface may be formed at a specified portion of the inner surface of the incubator hood 14.

(Hydrophilic Sheet)

Next, the explanation will be made on the hydrophilic sheet used to provide the hydrophilized portion at a specified portion of the inner surface of the incubator hood of the incubator of the invention.

Figure 3A:
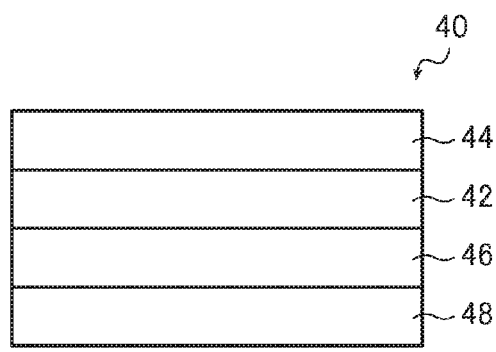
FIGS. 3A and 3B are schematic cross-sectional views each showing an example of a hydrophilic sheet used for providing a hydrophilized portion on the inner surface of an incubator hood of the incubator shown in FIG. 1.

A hydrophilic sheet 40 of the invention has a sheet body 42, a hydrophilized portion 44 formed on one of the outer surfaces of the sheet body 42, a pressure sensitive adhesive layer 46 formed on the other of the outer surfaces of the sheet body 42 opposite from the one of the outer surfaces, and a release sheet 48 laminated on a surface of the pressure sensitive adhesive layer 46 opposite from the side facing the sheet body 42 as shown in FIG. 3A.

Figure 3B:
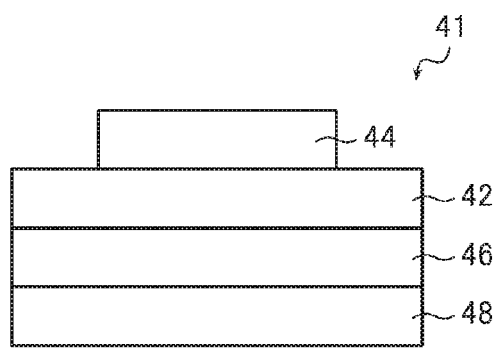

The hydrophilic sheet of the invention is not limited to the hydrophilic sheet 40 shown in FIG. 3A in which the hydrophilized portion 44 is formed over the entire area of the one of the outer surfaces of the sheet body 42 and may be a hydrophilic sheet 41 shown in FIG. 3B in which the hydrophilized portion 44 is formed on a part of the one of the outer surfaces of the sheet body 42.

The hydrophilic sheets 40 and 41 of the invention are each used to form the hydrophilized portion 44 on the inner surface of the incubator hood 14 of the incubator 10 of the invention by attaching the laminate having the hydrophilized portion 44 and the sheet body 42.

In the examples shown in FIGS. 3A and 3B, the hydrophilic sheets 40 and 41 each have the pressure sensitive adhesive layer 46 and therefore, when the release sheet 48 is peeled from the pressure sensitive adhesive layer 46 and the pressure sensitive adhesive layer 46 is attached onto the inner surface of the incubator hood 14 at a specified portion or the like that is a hydrophilized portion-forming area, the laminate having the hydrophilized portion 44 and the sheet body 42 can be adhered to the hydrophilized portion-forming area via the pressure sensitive adhesive layer 46, thereby disposing the hydrophilized portion 44 at the specified portion of the inner surface of the incubator hood 14.

While in the examples shown in FIGS. 3A and 3B, the hydrophilic sheets 40 and 41 each include the pressure sensitive adhesive layer 46 in addition to the laminate having the hydrophilized portion 44 and the sheet body 42, the present invention is not limited thereto and the hydrophilic sheet 40 or 41 may be constituted only by the laminate having the hydrophilized portion 44 and the sheet body 42. When the hydrophilic sheet 40 or 41 is constituted only by the laminate having the hydrophilized portion 44 and the sheet body 42, an adhesive or the like is applied on the hydrophilized portion-forming area or a surface of the sheet body 42 to form an adhesive layer or the like, and the laminate having the hydrophilized portion 44 and the sheet body 42 is attached to the hydrophilized portion-forming area, thereby forming the hydrophilized portion 44.

The hydrophilized portion 44 is the same as the above-mentioned hydrophilized portion and the explanation thereof is omitted.

The sheet body 42 supports the hydrophilized portion 44 formed over the entire area or on a part of the one of its outer surfaces. The hydrophilized portion 44 may be formed either over the entire area or on a part of the one of the outer surfaces of the sheet body 42 and is preferably formed over the entire area.

The main body 42 is not particularly limited as long as it can support the hydrophilized portion 44 and a sheet of any known type may be used. For example, use may be made of a polyethylene terephthalate (PET) film, a polybutylene terephthalate (PBT) film, a polyimide film, a triacetylcellulose film and the like. For the PET, Lumirror U34 of Toray Industries, Inc., Cosmoshine A4300 of Toyobo Co., Ltd., O3916W of Teijin Limited and the like can be used. The sheet body 42 may have on its surface an easily adhering layer.

The thickness of the sheet body 42 is not particularly limited and is preferably from 10 μm to 200 μm. When an object to which the hydrophilic sheet is attached is a touch panel of resistive membrane type, it is necessary to follow the flexible surface and therefore, the thickness of the sheet body 42 is preferably from 10 μm to 100 μm and more preferably from 10 μm to 50 μm. When the touch panel is of capacitive sensing type, the sheet body 42 having a thickness of 50 μm to 100 μm can be preferably used in terms of attachability.

The pressure sensitive adhesive layer 46 is used to attach the laminate having the hydrophilized portion 44 and the sheet body 42 to the hydrophilized portion-forming area corresponding to a specified portion of the inner surface of the incubator hood 14 described above. The pressure sensitive adhesive layer 46 is not particularly limited as long as it serves to attach the laminate having the hydrophilized portion 44 and the sheet body 42 to the hydrophilized portion-forming area, and may be formed using any known pressure sensitive adhesive. Exemplary pressure sensitive adhesives usable for the pressure sensitive adhesive layer 46 include, but not limited thereto, a (meth)acrylic pressure sensitive adhesive, a rubber pressure sensitive adhesive, a silicone pressure sensitive adhesive, an urethane pressure sensitive adhesive and a polyester pressure sensitive adhesive. When the pressure sensitive adhesive layer 46 is used for a surface of a touch panel, a pressure sensitive adhesive of self-adhesive type can be preferably used in view of repetitive attachment and detachment as well as attachment with no air bubbles. The (meth)acrylic pressure sensitive adhesive refers to an acrylic pressure sensitive adhesive and/or a methacrylic pressure sensitive adhesive. For the (meth)acrylic pressure sensitive adhesive, a (meth)acrylic pressure sensitive adhesive used for a pressure sensitive adhesive sheet to be described later may be used.

A method of forming the pressure sensitive adhesive layer is not particularly limited and examples thereof include a coating method, a printing method, an attaching method and the like. In particular, the method involving coating to thereby provide the pressure sensitive adhesive layer and the method involving attachment of a pressure sensitive adhesive sheet to thereby form the pressure sensitive adhesive layer are preferred, and the method involving attachment of a pressure sensitive adhesive sheet is more preferred.

The thickness of the pressure sensitive adhesive layer 46 is not particularly limited and is preferably from 1 μm to 30 μm. At a pressure sensitive adhesive layer thickness of 1 μm or more, this enables stable film formation by coextrusion and at a pressure sensitive adhesive layer thickness of 30 μm or less, the material cost is reduced. When high adhesion is required, the pressure sensitive adhesive layer preferably has a large thickness in view of its viscosity. This is because the contact area with an object to be covered tends to increase with increasing thickness of the pressure sensitive adhesive layer. The thickness of the pressure sensitive adhesive layer is preferably from 2 to 20 m, more preferably from 3 to 15 m.

The adhesion of the pressure sensitive adhesive layer 46 is also not particularly limited and is preferably from 2 cN/25 mm to 20 cN/25 mm in practice. At an adhesion of 2 cN/25 mm or more, the pressure sensitive adhesive layer 46 attached to a surface of a touch panel or the like in use is unlikely to come off. At an adhesion of 20 cN/25 mm or less, a film can be smoothly peeled.

The release sheet 48 adheres to the pressure sensitive adhesive layer 46 for protecting the pressure sensitive adhesive layer 46 until the hydrophilic sheet 40 is used. The release sheet 46 is not limited as long as it can protect the pressure sensitive adhesive layer 46 and any known release sheet may be used. For instance, use may be made of silicone-based compounds, long-chain alkyl-based compounds and parting agents such as polyvinyl alcohol•carbamate.

The thickness of the release sheet 48 is not particularly limited and is preferably from 1 μm to 30 μm. At a release layer thickness of 1 μm or more, this enables stable film formation by coextrusion and at a release layer thickness of 30 μm or less, the material cost is reduced. The thickness of the release layer is preferably from 2 μm to 20 μm and more preferably from 3 μm to 15 μm.

(Hydrophilic Antibacterial Film)

Next, the explanation will be made on a hydrophilic antibacterial film formed directly at a specified portion of the inner surface of the incubator hood of the incubator of the invention in order to provide the hydrophilized portion at the specified portion of the inner surface of the incubator hood.

Figure 4A:
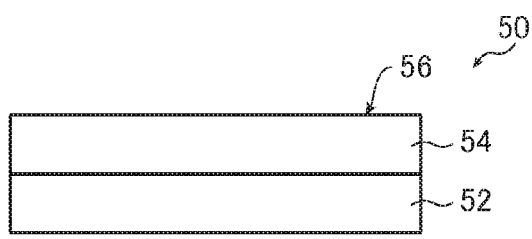
FIGS. 4A to 4C are schematic cross-sectional views each showing an example of a base having a hydrophilic antibacterial film provided directly on the inner surface of the incubator hood in order to provide the hydrophilized portion on the inner surface of the incubator hood of the incubator shown in FIG. 1.
Figure 4B:
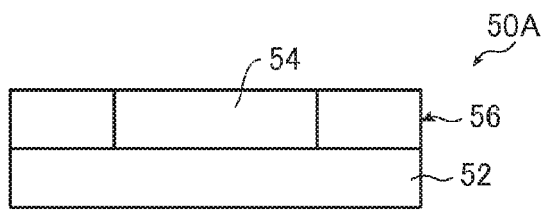
Figure 4C:
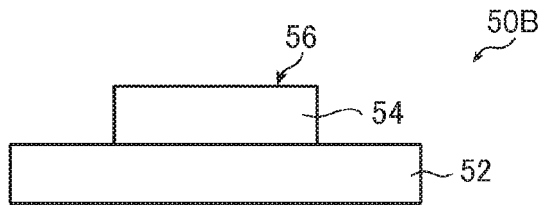

FIGS. 4A to 4C each show a base having a hydrophilic antibacterial film (hereinafter simply called "base having an antibacterial film") in which the hydrophilic antibacterial film is formed directly on a substrate that constitutes a specified portion of the housing of the incubator hood.

A base 50 having an antibacterial film shown in FIG. 4A includes a substrate 52 and a hydrophilic portion 54 formed on one of the outer surfaces (upper surface in the drawing) of the substrate 52, the hydrophilic portion 54 constituting a hydrophilic antibacterial film 56 of the invention.

The hydrophilic antibacterial film 56 of the invention is not limited to the one constituted by the hydrophilic portion 54 formed over the entire area of the one of the outer surfaces of the substrate 52 as shown in FIG. 4A and may be one formed over the entire area of the one of the outer surfaces of the substrate 52 so as to include the hydrophilic portion 54 formed on a part of the one of the outer surfaces of the substrate 52 in a base 50A having an antibacterial film as shown in FIG. 4B or one constituted by the hydrophilic portion 54 formed on a part of the one of the outer surfaces of the substrate 52 in a base 50B having an antibacterial film as shown in FIG. 4C.

The substrate 52 of the base 50, 50A or 50B having an antibacterial film shown in FIG. 4A, 4B or 4C is a member constituting the hydrophilized portion-forming area at a specified portion of the housing of the incubator hood 14. For example, the substrate 52 is a constituent member, e.g., a wall member, of the front surface part including the front part 14a and/or the inclined part 14b, and/or the inclined part 14b and the like, and in addition the back part 14d and/or the pair of side parts 14e of the incubator hood 14 shown in FIG. 1.

The hydrophilic portion 54 of the base 50, 50A or 50B having an antibacterial film shown in FIG. 4A, 4B or 4C is disposed on at least a part of the surface of the substrate 52. More specifically, the hydrophilic portion 54 may be disposed either over the entire area of one side of the substrate 52 as in the base 50 having an antibacterial film shown in FIG. 4A or only on a part of a surface of the substrate 52 as in the bases 50A and 50B each having an antibacterial film shown in FIGS. 4B and 4C. The substrate 52 may constitute the whole hydrophilic antibacterial film 56 as in the bases 50 and 50B each having an antibacterial film shown in FIGS. 4A and 4C or may constitute only a part of the hydrophilic antibacterial film 56 as in the base 50A having an antibacterial film shown in FIG. 4B.

It can be said that the hydrophilic portion 54 has totally the same configuration as that of the hydrophilized portion of the invention, i.e., the hydrophilized portion formed at a specified portion constituting at least a part of the inner surface of the incubator hood 14 described above, for instance, the hydrophilized portion 44 of the hydrophilic sheet 40 or 41 shown in FIG. 3A or 3B.

In short, the hydrophilic portion of the invention has totally the same configuration as that of the hydrophilized portion of the invention described above and therefore, the explanation thereof will not be made.

The hydrophilic antibacterial film 56 of the base 50, 50A or 50B having an antibacterial film shown in FIG. 4A, 4B or 4C is a film disposed on at least a part of a surface of the substrate 52 and having the antibacterial action. At least a part of the hydrophilic antibacterial film 56 has hydrophilicity. In other words, at least a part of the hydrophilic antibacterial film 56 is constituted by the hydrophilic portion 54.

Specifically, the hydrophilic antibacterial film 56 may be disposed either over the entire area of one side of the substrate 52 as in the bases 50 and 50A each having an antibacterial film shown in FIGS. 4A and 4B or only on a part of a surface of the substrate 52 as in the base 50B having an antibacterial film shown in FIG. 4C. The hydrophilic antibacterial film 56 may be configured so that the hydrophilic portion 54 constitutes either the whole hydrophilic antibacterial film 56 as in the bases 50 and 50B each having an antibacterial film shown in FIGS. 4A and 4C or only a part of the hydrophilic antibacterial film 56 as in the base 50A having an antibacterial film shown in FIG. 4B.

The hydrophilic antibacterial film contains the antibacterial agent contained in the hydrophilized portion described above, preferably at least one type of silver-containing antibacterial agent. The antibacterial agent and the silver-containing antibacterial agent (silver-based antibacterial agent) used here are the same as the antibacterial agent and the silver-based antibacterial agent described above and therefore, the explanation thereof will not be made.

In the present invention, the content of the antibacterial agent or the silver-based antibacterial agent described above in the hydrophilic antibacterial film is not particularly limited as with the case of the content in the hydrophilized portion. The antibacterial agent or the silver-based antibacterial agent is preferably contained in the hydrophilic antibacterial film at an antibacterial agent (or silver) content of 0.001 to 20 wt % (preferably from 0.001 to 5 wt %) with respect to the total weight of the hydrophilic antibacterial film because the effects of the invention are more excellent.

When an organic antibacterial agent is used as the antibacterial agent, especially as the silver-based antibacterial agent, the antibacterial agent content is not particularly limited and is preferably from 1 to 4 wt % with respect to the total weight of the antibacterial film because the antibacterial film exhibits higher mechanical strength and the effects of the invention are more excellent.

When an inorganic antibacterial agent is used as the antibacterial agent, especially as the silver-based antibacterial agent, the antibacterial agent content is not particularly limited and is preferably from 0.001 to 10 wt % and more preferably 0.01 to 5 wt % with respect to the total weight of the antibacterial film because the antibacterial film exhibits higher mechanical strength and the effects of the invention are more excellent.

It can be said that the base having an antibacterial film including the substrate and the hydrophilic antibacterial film described above is a base having a hydrophilic portion.

The incubator 10 according to this embodiment is basically configured as described above and subsequently, the effects thereof is described.

When a neonate is brought into the incubator 10 of the invention, the front door 18 at the front part 14a of the incubator hood 14 is pulled down to open the accommodating room 15, whereafter a medical professional holds the neonate with his/her hands, brings the neonate into the accommodating room 15 through the front door 18 opened to lay the neonate down on the bed prepared on the flat upper surface 12a of the base table 12, pulls out his/her hands from the accommodating room 15 through the front door 18 and then closes the front door 18 to allow the accommodating room 15 to be isolated from the outside.

Thereafter, a medical professional can insert his/her hands into the accommodating room 15 of the incubator 10 through the pair of arm holes 16 at the pair of side parts 14e or the pair of arm holes 20 at the front part 14a of the incubator hood 14 and give various treatments such as suckling, care and medical examination to the neonate as necessary.

In addition, the neonate can be taken out of the accommodating room 15 of the incubator 10 by opening the front door 18 as necessary.

The interior of the accommodating room 15 accommodating the neonate is maintained at a predetermined temperature (temperature slightly higher than room temperature at the outside of the incubator) by sending hot air having been cleaned by cleaning means and heated by heating means to flow through a space in a double structure in the wall of the incubator hood 14, at a predetermined humidity (considerably high humidity) by supplying heated steam having been cleaned by humidification means and at a predetermined oxygen concentration (oxygen concentration higher than that of the air) by supplying oxygen by oxygenation means, for example.

While the interior of the accommodating room 15 of the incubator hood 14 is thus maintained at a temperature higher than room temperature and at a considerably high humidity, the hydrophilized portion is provided on the inner surface of a specified portion of the incubator hood 14, for instance, the inner surface of the observation portion that allows the observation of the neonate accommodated in the accommodating room 15 from the outside and therefore, the occurrence of fog or condensation on the inner surface of the incubator hood 14 can be prevented or suppressed, so that the visibility of the interior of the accommodating room 15 of the incubator 10 from the outside does not deteriorate, whereby the neonate can be easily, reliably and carefully observed.

As a result, a medical professional can insert his/her hands into the accommodating room 15 of the incubator 10 through the pair of arm holes 16 or 20 at the incubator hood 14 and reliably and appropriately give various treatments such as suckling, care and medical examination to the neonate.

In addition, the hydrophilized portion has antibacterial properties and therefore, even when a neonate is brought into or taken out from the accommodating room 15 of the incubator 10 or the foregoing various treatments are performed with hands inserted from the arm holes at the incubator hood, bacteria and the like are unlikely to be attached and the growth of bacteria can be prevented or suppressed.

Even when a shade cover is covered on the incubator hood 14 so that light is blocked, the hydrophilized portion has a water contact angle of up to 30° and exhibits sufficient hydrophilicity as well as sufficient antifogging properties and antibacterial properties.

The hydrophilized portion on at least a part of the inner surface of the incubator hood 14 of the incubator 10 or preferably the entire inner surface of the incubator hood 14 may be cleaned at the start of use of the incubator 10 or after the use thereof. Specifically, the inner surface of the incubator hood 14 may be wiped with a wiper or the like soaked with an antiseptic solution. For the antiseptic solution, an ethanol aqueous solution or an aqueous solution of sodium hypochlorite is preferably used. The use of the ethanol aqueous solution or the like may deteriorate the quality of material of the incubator hood 14 and therefore, formalin is occasionally used.

Due to the hydrophilicity of the hydrophilized portion, the inner surface of the incubator hood 14 sufficiently gets wet with the antiseptic solution. In other words, the antiseptic solution sufficiently spreads out on the inner surface of the incubator hood 14. Accordingly, even if bacteria remain on the inner surface of the incubator hood by any chance at the time, the antiseptic solution comes in contact with the bacteria for a long period of time. In addition, the antibacterial agent is contained in the hydrophilized portion on the inner surface of the incubator hood 14 and acts on bacteria. Therefore, the bactericidal power can be improved more than ever and the growth of bacteria can be suppressed.

The incubator hood according to Embodiment 1 thus has excellent antifogging properties and antibacterial properties.

Embodiment 2

While in Embodiment 1, the type of the antibacterial agent contained in the hydrophilized portion is not particularly limited, a hydrophilized portion according to Embodiment 2 contains as the antibacterial agent at least a silver-containing first antibacterial agent (hereinafter also simply called "first antibacterial agent") and a silver-containing second antibacterial agent (hereinafter also simply called "second antibacterial agent") different from the first antibacterial agent. In other words, the hydrophilized portion contains at least two types of silver-containing antibacterial agents (hereinafter also simply called "silver-based antibacterial agent(s)"). Embodiments 1 and 2 have the same configuration and effects except that they are different in terms of the antibacterial agent.

The first and second antibacterial agents are not particularly limited for type as long as they contain silver (silver atom). The form of the silver is also not particularly limited and silver is contained in the form of metallic silver, silver ion, silver salt (including silver complex) or the like. In the present specification, the silver complex falls within the scope of the definition of the silver salt.

Exemplary silver salts include silver acetate, silver acetylacetonate, silver azide, silver acetylide, silver arsenite, silver benzoate, silver hydrogen fluoride, silver bromate, silver bromide, silver carbonate, silver chloride, silver chlorate, silver chromate, silver citrate, silver cyanate, silver cyanide, silver (cis,cis-1,5-cyclooctadiene)-1,1,1,5,5,5-hexafluoro acetylacetonate, silver diethyldithiocarbamate, silver(I) fluoride, silver(II) fluoride, silver 7,7-dimethyl-1,1,1,2,2,3,3-heptafluoro-4,6-octanedionate, silver hexafluoroantimonate, silver hexafluoroarsenate, silver hexafluorophosphate, silver iodate, silver iodide, silver isothiocyanate, silver potassium cyanide, silver lactate, silver molybdate, silver nitrate, silver nitrite, silver(I) oxide, silver(II) oxide, silver oxalate, silver perchlorate, silver perfluorobutyrate, silver perfluoropropionate, silver permanganate, silver perrhenate, silver phosphate, silver picrate monohydrate, silver propionate, silver selenate, silver selenide, silver selenite, silver sulfadiazine, silver sulphate, silver sulfide, silver sulfite, silver telluride, silver tetrafluoroborate, silver tetraiodo curiumate, silver tetratungstate, silver thiocyanate, silver p-toluenesulfonate, silver trifluorometanesulfonate, silver trifluoroacetate and silver vanadate.

Examples of the silver complex include histidine silver complex, methionine silver complex, cysteine silver complex, aspartate silver complex, pyrrolidonecarboxylate silver complex, oxotetrahydrofurancarboxylate silver complex and imidazole silver complex.

Examples of the first and second antibacterial agents include organic antibacterial agents such as the foregoing silver salts and inorganic antibacterial agents each containing a carrier described below, and the types thereof are not particularly limited.

In particular, the first and second antibacterial agents are each preferably composed of a silver-carrying carrier including a carrier and silver carried thereon in terms of exerting the antibacterial action in a short time and/or retaining the antibacterial properties over long periods (hereinafter also simply referred to as "in terms of further excellent effects of Embodiment 2").

The type of the carrier is not particularly limited and examples thereof include calcium zinc phosphate, calcium phosphate, zirconium phosphate, aluminum phosphate, calcium silicate, activated carbon, activated alumina, silica gel, zeolite, hydroxyapatite, titanium phosphate, potassium titanate, hydrous bismuth oxide, hydrous zirconium oxide and hydrotalcite. Examples of the zeolite include natural zeolites such as chabazite, mordenite, erionite and clinoptilolite and synthetic zeolites such as A-type zeolite, X-type zeolite and Y-type zeolite.

The average particle size of the silver-carrying carrier is not particularly limited and is preferably from 0.1 to 10 μm and more preferably 0.1 to 2.0 μm in terms of further excellent effects of Embodiment 2. The average particle size above is a value obtained by measuring the diameters of at least given ten silver-carrying carriers with a microscope and calculating the arithmetic mean of the measurements.

As described above, the silver may be contained in the form of any one of silver ion, metallic silver and silver salt.

A preferred embodiment of the second antibacterial agent is a silver-carrying carrier using a porous material (e.g., zeolite, zirconium phosphate, aluminum phosphate and calcium silicate) as a carrier.

In the most preferred embodiments of the first and second antibacterial agents, the first antibacterial agent preferably has silver and a carrier selected from the group consisting of calcium zinc phosphate and calcium phosphate and the second antibacterial agent preferably has silver and a carrier composed of zeolite in terms of further excellent effects of Embodiment 2. In other words, the first antibacterial agent is a silver-carrying catalyst having a carrier selected from the group consisting of calcium zinc phosphate and calcium phosphate as well as silver carried on the carrier, and the second antibacterial agent is a silver-carrying catalyst having a carrier composed of zeolite as well as silver carried on the carrier.

The silver contents in the first and second antibacterial agents are not particularly limited and in the case of the silver-carrying carrier described above for example, are each preferably from 0.1 to 30 wt % and more preferably from 0.3 to 10 wt % with respect to the total weight of the silver-carrying carrier.

The total content of the above-described first and second antibacterial agents in the hydrophilized portion is not particularly limited. The first and second antibacterial agents are preferably contained in the hydrophilized portion to allow the silver content to be 0.0001 to 1 wt % (preferably from 0.001 to 0.1 wt %) with respect to the total weight of the hydrophilized portion in terms of further excellent effects of Embodiment 2.

The silver content in the hydrophilized portion refers to the total silver content in the first and second antibacterial agents.

The first (or second) antibacterial agent content in the hydrophilized portion is not particularly limited and is preferably from 0.001 to 10 wt %, more preferably from 0.01 to 5 wt % and still more preferably 0.01 to 1 wt % with respect to the total weight of the hydrophilized portion in terms of higher mechanical strength of the hydrophilized portion and further excellent effects of Embodiment 2.

(Characteristics of Hydrophilized Portion and Method of Forming the Same)

The characteristics of the hydrophilized portion including the antibacterial agents described above and the method of forming the hydrophilized portion are the same as those in Embodiment 1.

(Base Having Hydrophilized Portion)

Figure 5:
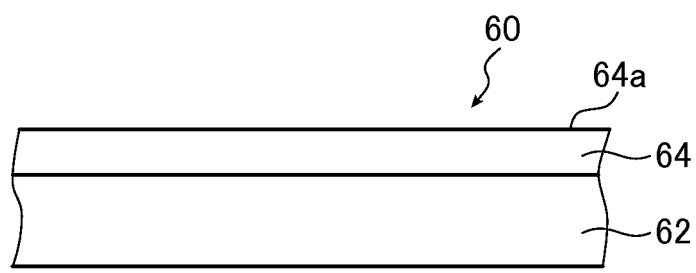
FIG. 5 is a schematic cross-sectional view showing an example of a base having a hydrophilized portion according to Embodiment 2 of the invention.

FIG. 5 shows a base having a hydrophilized portion according to Embodiment 2. A base 60 having a hydrophilized portion includes a substrate 62 and a hydrophilized portion 64 disposed on the substrate 62. An incubator hood of this embodiment has on its inner surface the base 60 having a hydrophilized portion. The hydrophilized portion 64 may be provided on at least a part of a surface of the substrate 62.

The base having a hydrophilized portion including the antibacterial agents described above satisfies the relations expressed by formulae (1) and (2) below when the silver content per unit area in the hydrophilized portion is represented by P (ng/cm$^2$) and the amount of silver ions per unit area as measured by an extraction test to be described later is represented by Q (ng/cm$^2$).

$$6.0 \leq P/Q \quad \text{Formula (1)}$$

$$15.0 \leq Q \quad \text{Formula (2)}$$

The base having a hydrophilized portion as described above can have antibacterial properties that are exhibited in a short time and retained over long periods.

The measurement methods of P and Q above will be described below in detail.

The silver content per unit area P (ng/cm$^2$) in the hydrophilized portion is a value obtained by dividing the amount of silver (ng) contained in the hydrophilized portion by the principal surface area (cm$^2$) of the hydrophilized portion. The principal surface area of the hydrophilized portion refers to the area of a principal surface 64a of the hydrophilized portion 64 opposite from the side facing the substrate 62 in FIG. 5.

A high silver content P means that a large amount of silver is contained in the hydrophilized portion. The silver content P is not particularly limited as long as it satisfies the relation expressed by formula (1) above and is preferably at least 90 ng/cm$^2$ and more preferably at least 120 ng/cm$^2$ in terms of further excellent effects of Embodiment 2. The upper limit of the silver content P is not particularly limited and is preferably up to 10000 ng/cm$^2$ and more preferably up to 1000 ng/cm$^2$ in terms of preventing color change or embrittlement of the film.

The measurement method of the silver content P is as follows: The amount of silver in the hydrophilized portion is measured by atomic absorption spectrometry (contrAA700 manufactured by Analytik Jena AG) with the use of the hydrophilized portion having a size adjusted to a predetermined size (area) and the amount of obtained silver is divided by the area above, thereby determining the silver content P. More specifically, silver contained in the hydrophilized portion is caused to be all eluted, the atomic absorption spectrometry is performed on the resultant solution, the silver amount is determined using a standard curve prepared beforehand, and the determined silver amount is divided by the area of the hydrophilized portion, thereby determining the silver content P. For the method of eluting all silver contained in the hydrophilized portion, use is made of wet ashing treatment that is commonly known as a pretreatment in inorganic analysis.

The extraction test uses 1/500 nutrient broth defined in JIS Z 2801:2010 as extraction liquid. The temperature of the extraction liquid is controlled to 35±1° C., and the hydrophilized portion (hydrophilized portion area: 4 cm$^2$ (2 cm×2 cm)) in the base having a hydrophilized portion is held in contact with the extraction liquid (liquid amount: 9 mL) for 1 hour. As the method of bringing the hydrophilized portion into contact with the extraction liquid, a method of immersing the base having a hydrophilized portion into the extraction liquid is employed.

Next, after the elapse of 1 hour, the base having a hydrophilized portion is recovered from the extraction liquid and the amount of silver ions (ng) extracted in the extraction liquid is measured. The amount of silver ions in the extraction liquid is measured by atomic absorption spectrometry (contrAA700 manufactured by Analytik Jena AG) and the silver ion amount is determined using a standard curve prepared beforehand In measuring the silver ion amount, nitric acid (about 1 mL) is preferably added to the extraction liquid as necessary in order to enhance measurement stability.

Subsequently, the determined silver ion amount is divided by the contact area of the hydrophilized portion with the extraction liquid (4 cm$^2$) to thereby obtain the silver ion amount per unit area Q (ng/cm$^2$). The contact area of the hydrophilized portion with the extraction liquid refers to the area of a surface of the hydrophilized portion in contact with the extraction liquid when the hydrophilized portion is held in contact with the extraction liquid and in the case of FIG. 5 for instance, the area of the principal surface 64a of the hydrophilized portion 64 opposite from the side facing the substrate 62.

The thus determined silver ion amount Q represents the degree of elution (extraction) of silver ions from the hydrophilized portion and satisfies the relation expressed by formula (2) below. Formula (2) means that Q is 15.0 ng/cm$^2$ or more.

$$15.0 \leq Q \quad \text{Formula (2)}$$

In particular, it is preferable to satisfy the relation expressed by formula (3) in terms of further excellent effects of Embodiment 2.

$$15.0 \leq Q \leq 25.0 \quad \text{Formula (3)}$$

Furthermore, the silver ion amount Q is preferably from 17.0 to 24.0 ng/cm$^2$ and more preferably from 19.0 to 21.0 ng/cm$^2$ in terms of further excellent effects of Embodiment 2.

At a silver ion amount Q of less than 15.0 ng/cm$^2$, short-term antibacterial properties are poor.

The silver content P and the silver ion amount Q described above satisfy the relation expressed by formula (1) below. Formula (1) means that P/Q is 6.0 or more. Note that P/Q expresses a value obtained by dividing P by Q.

$$6.0 \leq P/Q \qquad \text{Formula (1)}$$

P/Q is preferably at least 7.0 and more preferably at least 10.0 in terms of further excellent effects of Embodiment 2. The upper limit of P/Q is not particularly limited and is preferably up to 20.0 and more preferably up to 15.0 because continuing effects of antibacterial properties are saturated.

At P/Q of less than 6, antibacterial properties at a predetermined level cannot be exhibited over long periods.

In the meantime, in recent years, medical devices are required to exert the antibacterial action within a shorter time to increase the frequency of use.

Moreover, the medical devices are required to retain the antibacterial action over a longer period of time.

In other words, there is a demand for such an incubator hood that can exert the antibacterial action within a short time and at the same time, retain antibacterial properties over long periods.

The present inventors studied antibacterial layer-carrying substrates described in JP 09-131389 A and JP 2002-337277 A and found that neither of the substrates sufficiently satisfies the foregoing requirements and further improvements are necessary. The present inventors found that the base having a hydrophilized portion according to Embodiment 2 has sufficient antifogging properties, exhibits antibacterial properties in a short time and retains antibacterial properties over long periods.

Thus, according to this embodiment, it is possible to provide an incubator hood that exerts the antibacterial action in a short time, retains the antibacterial properties over long periods and has excellent antifogging properties, an incubator having the incubator hood, a hydrophilic sheet for incubators for use in forming the incubator hood, and a hydrophilic antibacterial film for incubators.

The substrate 62 and the hydrophilized portion 64 of the base 60 having a hydrophilized portion constitute the sheet body 42 and the hydrophilized portion 44 of the hydrophilic sheet 40 or the substrate 52 and the hydrophilic portion 54 of the base 50 having a hydrophilic antibacterial film (base 50 having an antibacterial film) according to Embodiment 1, respectively.

Embodiment 3

While in Embodiment 1, the type of the antibacterial agent contained in the hydrophilized portion is not particularly limited, a hydrophilized portion according to Embodiment 3 contains at least one type of silver as the antibacterial agent. In other words, Embodiments 1 and 3 have the same configuration and effects except that they are different in terms of the antibacterial agent.

In Embodiment 3, a silver-containing antibacterial agent (hereinafter also called "silver-based antibacterial agent") is not particularly limited for type as long as it contains silver (silver atom). Embodiments and specific examples of silver used in Embodiment 3 are the same as those in Embodiment 2.

Examples of the silver-based antibacterial agent include organic antibacterial agents such as silver salts (silver complexes) and inorganic antibacterial agents each containing a carrier, and the type thereof is not particularly limited.

In particular, the silver-based antibacterial agent is preferably composed of a silver-carrying carrier including a carrier and silver carried thereon in terms of more excellent light resistance and/or more excellent antibacterial properties at the hydrophilized portion (hereinafter also simply referred to as "in terms of further excellent effects of Embodiment 3").

The carrier used in Embodiment 3 is the same in type as that in Embodiment 2 and is preferably composed of ceramic in terms of further excellent effects of Embodiment 3.

The average particle size of the silver-carrying carrier used in Embodiment 3 is also the same as that in Embodiment 2.

The silver content in the silver-based antibacterial agent is not particularly limited and in the case of the silver-carrying carrier described above for example, is preferably from 0.1 to 10 wt % and more preferably 0.3 to 5 wt % with respect to the total weight of the silver-carrying carrier.

The silver-based antibacterial agent content in the hydrophilized portion is not particularly limited. The silver-based antibacterial agent is preferably contained in the hydrophilized portion to allow the silver content to be 0.001 to 20 wt % (preferably from 0.001 to 5 wt %) with respect to the total weight of the hydrophilized portion in terms of further excellent effects of Embodiment 3.

When an organic antibacterial agent is used as the silver-based antibacterial agent, the antibacterial agent content is not particularly limited and is preferably from 1 to 4 wt % with respect to the total weight of the hydrophilized portion in terms of higher mechanical strength of the hydrophilized portion and further excellent effects of Embodiment 3.

When an inorganic antibacterial agent is used as the silver-based antibacterial agent, the antibacterial agent content is not particularly limited and is preferably from 0.001 to 10 wt % and more preferably from 0.01 to 5 wt % with respect to the total weight of the hydrophilized portion in terms of higher mechanical strength of the hydrophilized portion and further excellent effects of Embodiment 3.

(Characteristics of Hydrophilized Portion)

The hydrophilized portion including the antibacterial agent described above has the same characteristics as those described in Embodiment 1 and is particularly excellent in visibility. Owing to the effects of the antibacterial agent, namely, the light resistant effect which serves to keep the color of the hydrophilized portion unchanged even after prolonged exposure to natural light and the excellent antifogging effect attributable to an water contact angle of up to 30° at a surface of the hydrophilized portion, the visibility of the transparent incubator hood is particularly excellent.

(Method of Forming Hydrophilized Portion)

The method of forming the hydrophilized portion including the antibacterial agent described above is the same as that in Embodiment 1.

(Base Having Hydrophilized Portion)

Figure 6:
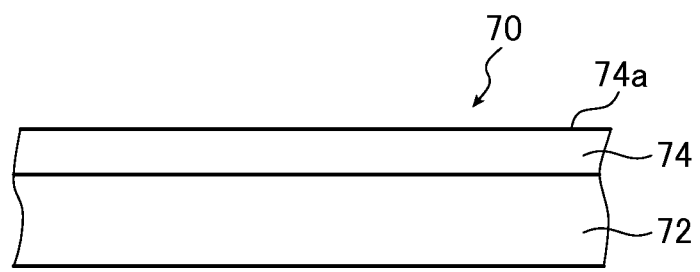
FIG. 6 is a schematic cross-sectional view showing an example of a base having a hydrophilized portion according to Embodiment 3 of the invention.

FIG. 6 shows a base having a hydrophilized portion according to Embodiment 3. A base 70 having a hydrophilized portion includes a substrate 72 and a hydrophilized portion 74 disposed on the substrate 72. An incubator hood of this embodiment has on its inner surface the base 70 having a hydrophilized portion. The hydrophilized portion 74 may be provided on at least a part of a surface of the substrate 72.

In the base 70 having a hydrophilized portion including the antibacterial agent described above, the silver ion amount per unit area as measured by an extraction test described below is from 15 to 50 ng/cm$^2$ and is preferably 15 to 40 ng/cm$^2$ and more preferably 15 to 30 ng/cm$^2$ in terms of further excellent effects of Embodiment 3.

At a silver ion amount of less than 15.0 ng/cm$^2$, the antibacterial properties are poor. At a silver ion amount in excess of 50 ng/cm$^2$, the light resistance is poor. In other words, the base having a hydrophilized portion (incubator hood) as described above can have excellent light resistance and exhibit antibacterial properties in a short time.

The method of the extraction test used in Embodiment 3 is the same as that in Embodiment 2.

In the meantime, in recent years, medical devices are required to exert the antibacterial action within a shorter time to increase the frequency of use.

In addition, an antibacterial layer-carrying substrate is exposed to illumination light or natural light for a long period of time and at that time, the antibacterial layer is required to keep its color unchanged. For instance, when the antibacterial layer on a surface of an incubator hood shows changes in color, this impairs the visibility of the interior of the incubator.

In other words, there is a demand for such an incubator hood that exerts the antibacterial action within a short time and at the same time, has excellent light resistance.

The present inventors studied the antibacterial layer-carrying substrates described in JP 09-131389 A and JP 2002-337277 A and found that the substrates do not sufficiently satisfy the foregoing requirements and further improvements are necessary. The present inventors found that the base having a hydrophilized portion according to Embodiment 3 can have sufficient antifogging properties, visibility and light resistance and exhibit antibacterial properties in a short time.

Thus, according to this embodiment of the invention, it is possible to provide an incubator hood excellent in antibacterial properties that has antifogging properties and light resistance and exerts the antibacterial action in a short time, an incubator having the incubator hood, a hydrophilic sheet for incubators for use in forming the incubator hood, and a hydrophilic antibacterial film for incubators.

The substrate 72 and the hydrophilized portion 74 of the base 70 having a hydrophilized portion constitute the sheet body 42 and the hydrophilized portion 44 of the hydrophilic sheet 40 or the substrate 52 and the hydrophilic portion 54 of the base 50 having a hydrophilic antibacterial film (base 50 having an antibacterial film) according to Embodiment 1, respectively.

Embodiment 4

Figure 7:
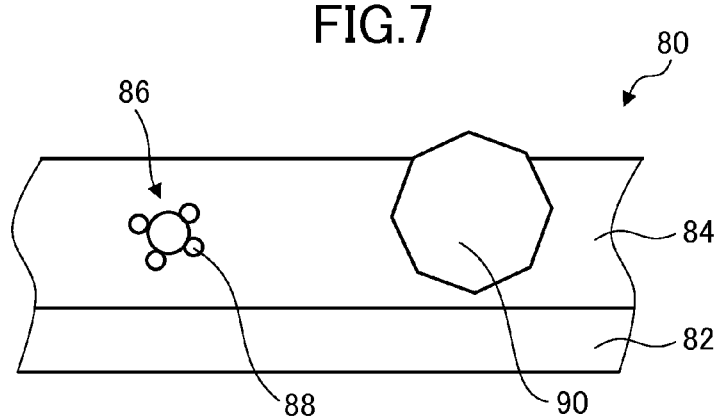
FIG. 7 is a schematic cross-sectional view showing an example of a base having a hydrophilized portion according to Embodiment 4 of the invention.

FIG. 7 shows a base having a hydrophilized portion according to Embodiment 4. A base 80 having a hydrophilized portion includes a substrate 82 and a hydrophilized portion 84 disposed on the substrate 82. An incubator hood of this embodiment has the base 80 having a hydrophilized portion on at least a part of its inner surface. The hydrophilized portion 84 includes an antibacterial agent 86 containing silver 88 and a porous carrier 90 capable of adsorbing silver ions.

While in Embodiment 1, the hydrophilized portion includes the hydrophilic polymer and the antibacterial agent, the hydrophilized portion according to Embodiment 4 includes a hydrophilic polymer, a silver-containing antibacterial agent and a porous carrier capable of adsorbing silver ions.

In the base having a hydrophilized portion according to Embodiment 4, the average particle size Da (μm) of the antibacterial agent and the average particle size Db (μm) of the porous carrier respectively satisfy the relations expressed by formulae (4) and (5) below with the average thickness T (μm) of the hydrophilized portion.

$$T/Da > 3.0 \quad \text{Formula (4)}$$

$$T/Db \leq 3.0 \quad \text{Formula (5)}$$

As shown in FIG. 7, the antibacterial agent 86 satisfying the requirement expressed by formula (4) above is often buried in the hydrophilized portion 84 and the porous carrier 90 satisfying the requirement expressed by formula (5) tends to be exposed at a surface of the hydrophilized portion 84.

Embodiments 1 and 4 have the same configuration and effects except that they are different in terms of the hydrophilized portion.

This embodiment is described below in detail.

(Hydrophilic Polymer)

The hydrophilic polymer is the same as that in Embodiment 1.

(Silver-Containing Antibacterial Agent)

The silver-containing antibacterial agent (hereinafter also called "silver-based antibacterial agent") is not particularly limited for type as long as it contains silver (silver atom). Embodiments and specific examples of silver used in Embodiment 4 are the same as those in Embodiment 2.

Examples of the silver-based antibacterial agent include organic antibacterial agents such as silver salts and inorganic antibacterial agents each containing a carrier, and the type thereof is not particularly limited.

In particular, the antibacterial agent is preferably composed of a silver-carrying carrier including a carrier and silver carried thereon in terms of exhibiting antibacterial properties in a short time and/or retaining antibacterial properties over long periods (hereinafter also simply referred to as "in terms of further excellent effects of Embodiment 4"). The type of the carrier used in Embodiment 4 is the same as that in Embodiment 2.

The average particle size of the antibacterial agent (preferably, the silver-carrying carrier) is not particularly limited as long as it satisfies the requirement expressed by formula (4) described above and is preferably from 0.1 to 10 μm, more preferably 0.1 μm or more but less than 2.0 μm and even more preferably from 0.3 to 1.0 μm in terms of further excellent effects of Embodiment 4.

The average particle size above is determined by measuring the 50% volume cumulative diameter (D50) three times with a laser diffraction/scattering particle size distribution analyzer manufactured by Horiba, Ltd. and averaging the three measurements.

In Embodiment 4, one of preferred embodiments of the silver-based antibacterial agent is an antibacterial agent containing silver and a carrier selected from the group consisting of calcium zinc phosphate and calcium phosphate in terms of further excellent effects of the invention. In other words, the antibacterial agent is preferably a silver-carrying catalyst containing a carrier selected from the group consisting of calcium zinc phosphate and calcium phosphate as well as silver carried on the carrier.

(Porous Carrier Capable of Adsorbing Silver Ions)

The porous carrier capable of adsorbing silver ions refers to a carrier having a number of pores capable of adsorbing silver ions and is not particularly limited for pore diameter, pore shape, pore volume, pore density, specific surface area and the like. Specifically, inorganic porous carriers such as activated carbon, zeolite, activated carbon fiber, silica gel, activated clay, alumina and diatomaceous earth and organic polymeric porous carriers such as pulp, fiber, paper, cloth, nonwoven fabric, wood and wood powder may be arbitrarily used. Examples of the zeolite include natural zeolites such as chabazite, mordenite, erionite and clinoptilolite and synthetic zeolites such as A-type zeolite, X-type zeolite and Y-type zeolite.

Silver may be carried on the porous carrier described above. Specifically, use may be made of a silver-carrying porous substance containing the porous carrier and silver carried thereon (corresponding to a so-called antibacterial agent). When silver is carried on the porous carrier (i.e., when the silver-carrying porous substance is included), the porous carrier carrying silver is different in type from the above-described antibacterial agent.

As described above, the hydrophilized portion includes one (porous substance) selected from the group consisting of the porous carrier capable of adsorbing silver ions and the silver-carrying porous carrier capable of adsorbing silver ions.

The silver carried on the porous carrier may be contained in the form of any one of silver ion, metallic silver and silver salt.

In particular, the hydrophilized portion preferably includes the silver-carrying porous carrier in terms of further excellent effects of Embodiment 4. In other words, the hydrophilized portion preferably includes the silver-carrying porous substance containing silver and the porous carrier. A preferred example of the porous carrier is zeolite. Specifically, it is preferable to include the silver-carrying catalyst containing the carrier composed of zeolite as well as silver carried on the carrier.

The average particle size of the porous carrier capable of adsorbing silver ions is not particularly limited as long as it satisfies the requirement expressed by formula (5) described above and is preferably from 0.1 to 20 μm, more preferably from 1.0 to 10 μm and even more preferably from 2.0 to 5.0 μm because the effects of the invention are more excellent.

The average particle size above is determined by measuring the 50% volume cumulative diameter (D50) three times with a laser diffraction/scattering particle size distribution analyzer manufactured by Horiba, Ltd. and calculating the average of the three measurements.

(Characteristics of Hydrophilized Portion and Method of Forming the Same)

The characteristics of the hydrophilized portion including the antibacterial agent and the porous carrier described above and the method of forming the hydrophilized portion are the same as those in Embodiment 1.

(Base Having Hydrophilized Portion)

As described above, in the base 80 having a hydrophilized portion including the antibacterial agent described above (incubator hood), the average particle size Da (μm) of the antibacterial agent and the average particle size Db (μm) of the porous carrier respectively satisfy the relations expressed by formulae (4) and (5) below with the average thickness T (μm) of the hydrophilized portion.

$$T/Da > 3.0 \quad \text{Formula (4)}$$

$$T/Db \leq 3.0 \quad \text{Formula (5)}$$

The base having a hydrophilized portion as described above can have antibacterial properties that are exhibited in a short time and retained over long periods.

Formula (4) above means that the ratio between the average thickness T of the hydrophilized portion and the average particle size Da of the antibacterial agent (T/Da) is more than 3.0. In particular, the ratio (T/Da) is preferably at least 3.1 and more preferably at least 3.2 in terms of further excellent effects of Embodiment 4. While being not particularly limited, the upper limit of the ratio (T/Da) is often up to 10 in general and is preferably up to 6.0 in terms of further excellent effects of Embodiment 4. When the relation expressed by formula (4) above is satisfied, the antibacterial agent tends to be buried in the hydrophilized portion, so that silver ions are inhibited from being excessively dissolved and released from the hydrophilized portion.

Formula (5) above means that the ratio between the average thickness T of the hydrophilized portion and the average particle size Db of the porous carrier (T/Db) is up to 3.0. In particular, the ratio (T/Db) is preferably up to 2.5 and more preferably up to 2.0 in terms of further excellent effects of Embodiment 4. The lower limit of the ratio (T/Db) is not particularly limited and is preferably at least 1.0 because the hydrophilized portion is further excellent in flatness. When the relation expressed by formula (5) above is satisfied, the porous carrier tends to protrude from a surface of the hydrophilized portion and this facilitates adsorption of silver ions.

The relation between the average particle size Da of the antibacterial agent and the average particle size Db of the porous carrier is not particularly limited. The ratio between the average particle size Db and the average particle size Da (Db/Da) is preferably up to 4.5 and preferably satisfies the relation expressed by formula (6) below in terms of further excellent effects of Embodiment 4.

$$Db/Da \leq 3.5 \quad \text{Formula (6)}$$

The lower limit of Db/Da is not particularly limited and is preferably at least 1.0 and more preferably at least 2.0 in terms of further excellent effects of Embodiment 4.

The silver content in the antibacterial agent is not particularly limited and in the case where the antibacterial agent is the silver-carrying carrier for example, is preferably from 0.1 to 30 wt % and more preferably 0.3 to 10 wt % with respect to the total weight of the silver-carrying carrier.

When silver is carried on the porous carrier, the amount of carried silver is not particularly limited and is preferably from 0.1 to 30 wt % and more preferably 0.3 to 10 wt % with respect to the total weight of the silver and the porous carrier.

The total content of the antibacterial agent and the porous carrier described above in the hydrophilized portion is not particularly limited. The antibacterial agent and the porous carrier are preferably contained in the hydrophilized portion to allow the silver content to be 0.0001 to 1 wt % and preferably from 0.001 to 0.1 wt % with respect to the total weight of the hydrophilized portion in terms of further excellent effects of Embodiment 4.

The silver content in the hydrophilized portion refers to the total amount of silver in the antibacterial agent and silver carried on the porous carrier.

The antibacterial agent content in the hydrophilized portion is not particularly limited and is preferably from 0.001 to 10 wt %, more preferably from 0.01 to 5 wt %, still more preferably 0.01 to 2.5 wt % and particularly preferably more than 1.0 wt % but not more than 2.5 wt % with respect to the total weight of the hydrophilized portion in terms of higher mechanical strength of the hydrophilized portion and further excellent effects of Embodiment 4.

The porous carrier content in the hydrophilized portion is not particularly limited and is preferably up to 10 wt %, more preferably up to 5 wt %, still more preferably up to 0.8 wt % and particularly preferably up to 0.5 wt % with respect to the total weight of the hydrophilized portion in terms of further excellent effects of Embodiment 4. The lower limit of the porous carrier content is not particularly limited and is preferably at least 0.001 wt % and more preferably at least 0.01 wt %.

Figure 8A:
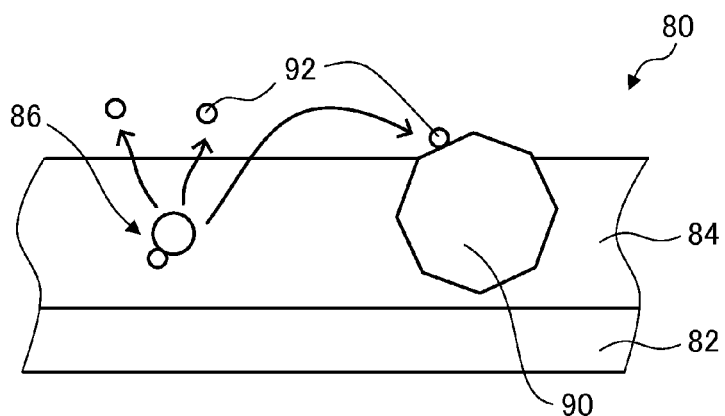
FIGS. 8A and 8B are views for explaining the mechanism of antibacterial properties of the base having a hydrophilized portion according to Embodiment 4 of the invention.
Figure 8B:
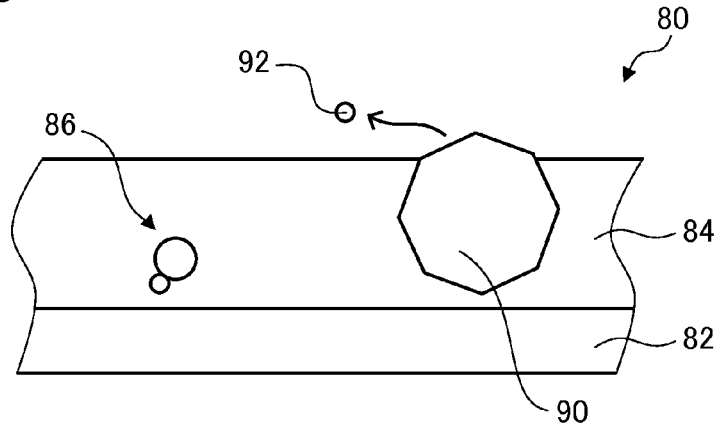

Next, the explanation is made on the mechanism how the base 80 having a hydrophilized portion according to Embodiment 4 exhibits antibacterial properties with reference to FIGS. 8A and 8B.

First, as shown in FIG. 8A, the silver 88 in the antibacterial agent 86 is ionized so that silver ions 92 are dissolved and released from the hydrophilized portion 84 and act on bacteria or the like on the hydrophilized portion 84. At that time, a part of the released silver ions 92 do not act on bacteria but are adsorbed to a surface of the porous carrier 90. The silver ions 92 are continuously dissolved and released from the antibacterial agent 86 and accordingly, the silver content in the antibacterial agent 86 is decreased and the amount of released silver ions is reduced, whereupon, as shown in FIG. 8B, the silver ions 92 having been adsorbed to the porous carrier 90 start to be dissolved and released to the outside in order to keep the balance of silver ions, so that antibacterial properties are retained. In other words, the porous carrier 90 included in the hydrophilized portion 84 serves to temporarily hold the silver ions 92 having been released from the antibacterial agent 86 whereby the silver ions 92 can again be dissolved and released after the elapse of a predetermined period of time (after the amount of silver ions released from the antibacterial agent 86 is reduced). Thus, compared to the case of not having the porous carrier 90, antibacterial properties can be retained over longer periods.

In the meantime, in recent years, medical devices are required to exert the antibacterial action within a shorter time to increase the frequency of use.

Moreover, the medical devices are required to retain the antibacterial action over a longer period of time.

In other words, there is a demand for such an incubator hood that can exert the antibacterial action within a short time and at the same time, retain antibacterial properties over long periods.

The present inventors studied antibacterial layer-carrying substrates described in JP 09-131389 A and JP 2002-337277 A and found that neither of the substrates sufficiently satisfies the foregoing requirements and further improvements are necessary. The present inventors found that the base having a hydrophilized portion (incubator hood) according to Embodiment 4 has sufficient antifogging properties, exhibits antibacterial properties in a short time and retains antibacterial properties over long periods.

Thus, according to this embodiment, it is possible to provide an incubator hood that exerts the antibacterial action in a short time, retains antibacterial properties over long periods and has antifogging properties, an incubator having the incubator hood, a hydrophilic sheet for incubators for use in forming the incubator hood, and a hydrophilic antibacterial film for incubators.

The substrate 82 and the hydrophilized portion 84 of the base 80 having a hydrophilized portion constitute the sheet body 42 and the hydrophilized portion 44 of the hydrophilic sheet 40 or the substrate 52 and the hydrophilic portion 54 of the base 50 having a hydrophilic antibacterial film (base 50 having an antibacterial film) according to Embodiment 1, respectively.

EXAMPLES

Example 1

In the incubator 10, an antibacterial agent-containing, hydrophilized portion-forming composition described below was applied on the inner surface of the front surface part, i.e., the front part 14a and the inclined part 14b of the incubator hood 14 and cured (by UV irradiation) to thereby provide an antibacterial agent-containing, antibacterial-treated hydrophilized portion. The hydrophilized portion had an average thickness of about 2 μm.

(Hydrophilized Portion-Forming Composition)

The composition included the ingredients described below. The amount of a silver ceramic particle dispersion for use as described below was adjusted to allow the silver ceramic particle content to be 0.5 wt % in the hydrophilized portion to be formed (content (wt %) with respect to the total weight of the hydrophilized portion).

Monomer having a hydrophilic group: Miramer M4004 (Toyo Chemicals co., Ltd.) 74 parts by weight Antibacterial agent: Silver ceramic particle dispersion (Fuji Chemical Industries, Ltd., average particle size: 0.8 μm)

Cross-linking agent: A-DPH (Shin-Nakamura Chemical Co., Ltd.) 20 parts by weight Polymerization initiator: IRGACURE (BASF) 3 parts by weight Example 2

Example 1 was repeated except that in place of the silver ceramic particles, a silver fine particle dispersion (Japan Ion Corporation, average particle size: 10 nm) was used as the antibacterial agent in the hydrophilized portion-forming composition and the amount of the silver fine particle dispersion was adjusted to allow the silver fine particle content to be 0.002 wt % in the hydrophilized portion to be formed (content (wt %) with respect to the total weight of the hydrophilized portion), thereby providing a hydrophilized portion.

Comparative Example 1

Example 1 was repeated except that Miramer M420 was used in place of the monomer having a hydrophilic group, thereby providing a hydrophilized portion. This monomer has no hydrophilic group.

Comparative Example 2

Example 1 was repeated except that no antibacterial agent was used, thereby providing a hydrophilized portion.

Example 3

Example 1 was repeated except that 3 parts by weight of a glidant having an average particle size of 8 μm was added to the hydrophilized portion-forming composition and in place of the silver ceramic particles, a bis(2-pyridylthio-1-oxide)zinc (ZPT) dispersion (Daiwa Chemical Industries Co., Ltd.) was contained as the antibacterial agent at an antibacterial agent (ZPT) content of 0.5 wt % with respect to the hydrophilized portion, thereby providing a hydrophilized portion.

Example 4

Example 3 was repeated except that the amount of the bis(2-pyridylthio-1-oxide)zinc (ZPT) dispersion used was changed to allow the antibacterial agent content to be 2.5 wt % instead of 0.5 wt %, thereby providing a hydrophilized portion.

Example 5

Example 3 was repeated except that the amount of the bis(2-pyridylthio-1-oxide)zinc (ZPT) dispersion used was changed to allow the antibacterial agent content to be 5 wt % instead of 0.5 wt %, thereby providing a hydrophilized portion.

Comparative Example 3

Example 3 was repeated except that the amount of the bis(2-pyridylthio-1-oxide)zinc (ZPT) dispersion used was changed to allow the antibacterial agent content to be 9 wt % instead of 0.5 wt %, thereby providing a hydrophilized portion.

The following various evaluations were made using the incubator having the incubator hood obtained in each of Examples 1 to 5 and Comparative Examples 1 to 3 described above.

The water contact angle of the hydrophilized portion on the incubator hood of the incubator obtained in each of Examples 1 to 5 and Comparative Examples 1 to 3 was measured by the above-described method. The results are all shown in Table 1.

<Evaluations>
(Antibacterial Properties)

The antibacterial activity was measured by the evaluation method described in JIS Z 2801 to evaluate antibacterial properties according to the criteria below. A higher antibacterial activity means more excellent antibacterial properties. An antibacterial activity of less than 2.0 was defined as "no antibacterial properties" and rated C; An antibacterial activity of 2.0 or more but less than 5.73 was defined as "having antibacterial properties" and rated B; and an antibacterial activity of 5.73 or more was defined as "excellent antibacterial properties" and rated A.

The antibacterial properties 3 hours after contact with a bacterial suspension were also evaluated in the same manner. The results are all shown in Table 1. The expression "antibacterial properties 3 hours after contact with a bacterial suspension" refers to antibacterial properties evaluated according to the foregoing criteria after the hydrophilized portion was allowed to remain in contact with the bacterial suspension for 3 hours.

The bacterial strain used was *Escherichia coli*.

"Antibacterial agent content" in Table 1 refers to the antibacterial agent content (wt %) with respect to the total weight of the hydrophilized portion.

(Antifogging Properties)

The environment in the accommodating room of the incubator obtained in each of Examples 1 to 5 and Comparative Examples 1 to 3 was maintained at a temperature of 35° and a humidity of 95% for 1 hour to conduct a high-temperature and high-humidity test of the incubator, and five researchers performed visual evaluation on the visibility of the hydrophilized portion on the incubator hood of the incubator.

In the visual evaluation on the visibility, the case where no fog was seen at all at the hydrophilized portion on the incubator hood was rated A; the case where fog was slightly seen but this did not affect the visibility of the interior of the accommodating room at all was rated B; the case where fog was seen a little but this did not affect the visibility of the interior of the accommodating room and the interior of the accommodating room was sufficiently observable was rated C; the case where fog was seen and the visibility of the interior of the accommodating room was poor, so that the observation of the interior of the accommodating room was hampered, was rated D; and the case where in addition to fog, condensation was seen and the visibility of the interior of the accommodating room was very poor, so that the observation of the interior of the accommodating room was impossible, was rated E.

The results are all shown in Table 1.

TABLE 1

| | Hydrophilized portion | | | | Evaluation | | |
|---|---|---|---|---|---|---|---|
| | Type of polymer | Type of anti-bacterial agent | Anti-bacterial agent content | Water contact angle | Anti-bacterial properties | Anti-bacterial properties 3 hours after contact with bacterial suspension | Anti-fogging properties |
| Example 1 | Hydrophilic polymer | Silver ceramic | 0.5 wt % | 8° | A | A | A |
| Example 2 | Hydrophilic polymer | Silver fine particles | 0.002 wt % | 8° | A | A | A |
| Example 3 | Hydrophilic polymer | ZPT | 0.5 wt % | 14° | B | B | A |
| Example 4 | Hydrophilic polymer | ZPT | 2.5 wt % | 20° | A | B | B |
| Example 5 | Hydrophilic polymer | ZPT | 5 wt % | 27° | A | B | B |
| Comparative Example 1 | Hydrophobic polymer | Silver ceramic | 0.5 wt % | 80° | A | C | D |
| Comparative Example 2 | Hydrophilic polymer | — | — | 7° | C | C | A |
| Comparative Example 3 | Hydrophilic polymer | ZPT | 9 wt % | 35° | A | B | C |

As can be seen from Table 1, there were made the evaluations for Comparative Examples 1 to 3 in which the hydrophilized portion has no antibacterial properties or has poor visibility and low antifogging properties while it was confirmed that in Examples 1 to 5, the antibacterial properties are excellent owing to the antibacterial agent included in the hydrophilized portion and since a superhydrophilic film at the hydrophilized portion serves to uniformly scatter water droplets on a film surface and thereby form a water film of a uniform thickness, the visibility is not or only a little affected and accordingly, the observation of a neonate in the accommodating room is not adversely affected. Since the hydrophilized portion thus exhibits excellent antibacterial properties, the antibacterial agent acts on trace amounts of pathogenic bacteria remaining on a surface to thereby suppress the growth of bacteria or sterilize the surface, thus lowering the possibility of infection by the medium of the surface of the incubator.

As is evident from Examples 1 to 5, it was confirmed that the antibacterial agent content falling within a predetermined range (0.001 to 5 wt %) leads to further excellent antibacterial properties.

From above results, the effects of Embodiment 1 of the invention are apparent.

Examples 6 to 10 and Comparative Examples 4 to 6

Preparation of Curable Composition

The following ingredients were mixed to prepare a curable composition.
Hydrophilic monomer: Miramer M4004 (Toyo Chemicals co., Ltd.) 76 parts by weight
Cross-linking agent: A-DPH (Shin-Nakamura Chemical Co., Ltd.) 21 parts by weight
Polymerization initiator: IRGACURE (BASF) 3 parts by weight
Solvent ingredient (No. 1): Methyl alcohol 15 parts by weight
Solvent ingredient (No. 2): Propylene glycol monomethyl ether 35 parts by weight
(Preparation of Antibacterial Agent)
(First Antibacterial Agent: Antibacterial Agent Containing Silver Carried on Calcium Zinc Phosphate)

Calcium hydroxide, zinc oxide and phosphoric acid were reacted to obtain phosphate. Silver nitrite was added to the phosphate, followed by washing, filtration, drying and fracturing, thereby obtaining a first antibacterial agent (silver-carrying carrier). The resultant first antibacterial agent had an average particle size of 1 μm and a silver ion content equivalent to 3 wt %.
(Second Antibacterial Agent: Antibacterial Agent Containing Silver Carried on Zeolite)

Zeolite was brought into contact with an aqueous silver nitrite solution to substitute silver ions for ion-exchangeable ions in the zeolite, thereby obtaining a second antibacterial agent. The resultant second antibacterial agent had an average particle size of 1.51 μm and a silver ion content equivalent to 0.5 wt %.

EXAMPLES AND COMPARATIVE EXAMPLES

The first and second antibacterial agents were added and mixed according to the relevant proportions (parts by weight) shown in Table 2 with respect to 100 parts by weight of the total solids in the curable composition prepared above, thereby preparing a hydrophilized portion-forming curable composition.
<Evaluations>
(1) Antibacterial Properties The resultant hydrophilized portion-forming curable composition was applied to a polycarbonate sheet (Carboglass CFR110C, manufactured by Asahi Glass Co., Ltd.) and dried at 60° C. for 30 minutes, whereafter a monomer was cured by UV irradiation, thereby forming a hydrophilized portion to produce an evaluation sample (base having a hydrophilized portion).

The evaluations described below were carried out using the resultant evaluation samples of Examples and Comparative Examples. The results are all shown in Table 2.
(Measurement of Silver Content P)

Each of the foregoing evaluation samples produced in Examples and Comparative Examples was cut to allow the hydrophilized portion size (area) to be 25 $cm^2$. Subsequently, the resultant sample piece was subjected to wet asking treatment, whereafter the silver content (ng) was determined by atomic absorption spectrometry (contrAA700 manufactured by Analytik Jena AG) with the use of a standard curve prepared beforehand and divided by the area of the hydrophilized portion, thereby determining the silver content P ($ng/cm^2$).
(Measurement of Silver Ion Amount Q)

Each of the foregoing evaluation samples produced in Examples and Comparative Examples was cut to allow the hydrophilized portion size (area) to be 4 $cm^2$. The cut evaluation sample was immersed in 9 ml of bacterial suspension (1/500 nutrient broth defined in JIS Z 2801:2010) at 35° C. for 1 hour. Then, 1 ml of nitric acid was added to this bacterial suspension, whereafter the silver ion amount was determined by atomic absorption spectrometry (contrAA700 manufactured by Analytik Jena AG) with the use of a standard curve prepared beforehand and divided by the area of the hydrophilized portion, thereby determining the silver ion amount Q ($ng/cm^2$).
(Evaluation on Initial Antibacterial Properties)

While the evaluation on antibacterial properties was based on the evaluation method defined in JIS Z 2801:2010, the test was conducted with a contact time with a bacterial suspension of 1 hour instead of 24 hours. The number of bacteria ($cell/cm^2$) after the test was measured with each sample and the evaluation was made according to the criteria below. The bacterial strain used was *Escherichia coli*. In order to confirm that the test proceeds successfully, the evaluation was simultaneously made with a polycarbonate sheet (Carboglass CFR110C, manufactured by Asahi Glass Co., Ltd.) provided with no hydrophilic portion and it was confirmed that the number of bacteria ($cell/cm^2$) after 1-hour contact was $6.2 \times 10^2$ ($cell/cm^2$) or more. "A" or "B" is preferred in practical use.
A: The number of bacteria was less than 1 $cell/cm^2$.
B: The number of bacteria was 1 $cell/cm^2$ or more but less than 10 $cell/cm^2$.
C: The number of bacteria was 10 $cell/cm^2$ or more.
(Evaluation on Antibacterial Properties after Durability Test)

The durability test was conducted as described below for the purpose of evaluating whether each evaluation sample prepared by the foregoing procedure exhibits antibacterial properties over long periods. In general, the hydrophilized portion disposed on a surface of a member is, when gets dirty, wiped with a wet cloth in most cases and at this time, silver is dissolved and released into water. This is the main cause of impairing antibacterial properties. Therefore, if excellent antibacterial properties are exhibited even after the following abrasion test, this proves that antibacterial properties can be retained over long periods even after the use of the hydrophilized portion.

In the durability test, each evaluation sample (base having a hydrophilized portion) prepared by the foregoing procedure was rubbed 36,000 times with a compress under a load of 500 g applied to the hydrophilized portion surface and thereafter, the test for evaluating antibacterial properties was conducted by the above-described method and the evaluation was made according to the criteria below. The bacterial strain used was *Escherichia coli*. The compress used was a polyester fabric (product name: Anticon) soaked in pure water. "A" or "B" is preferred in practical use.
A: The number of bacteria was less than 1 cell/cm$^2$.
B: The number of bacteria was 1 cell/cm$^2$ or more but less than 10 cell/cm$^2$.
C: The number of bacteria was 10 cell/cm$^2$ or more.

"Silver content rate (wt %)" in Table 1 refers to the proportion (wt %) of silver contained in the hydrophilized portion with respect to the total weight of the hydrophilized portion.

(2) Antifogging Properties

In the incubator 10, the resultant hydrophilized portion-forming curable composition was applied on the inner surface of the front surface part, i.e., the front part 14a and the inclined part 14b of the incubator hood 14 and cured (by UV irradiation) to thereby provide an antibacterial agent-containing, antibacterial-treated hydrophilized portion. The hydrophilized portion had an average thickness of about 2 μm.

The water contact angle of the hydrophilized portion on the incubator hood of the incubator obtained in each of Examples and Comparative Examples was measured by the above-described method. The results are all shown in Table 2.

The method of evaluating antifogging properties is the same as the evaluation method used for Examples 1 to 5 and Comparative Examples 1 to 3 described above.
The results are all shown in Table 2.

Examples 11 to 15 and Comparative Examples 7 to 9

Preparation of Antibacterial Agent

A silver ceramic particle dispersion (Fuji Chemical Industries, Ltd., average particle size: 0.8 μm) was added and mixed into the curable composition prepared in the same manner as in Examples 6 to 10 and Comparative Examples 4 to 6 described above according to the relevant proportion shown in the "Antibacterial agent weight" field in Table 3, thereby preparing a hydrophilized portion-forming curable composition.

<Evaluations>
(1) Evaluation on Antibacterial Properties and Light Resistance

The resultant hydrophilized portion-forming curable composition was applied to a polycarbonate sheet (Carboglass CFR110C, manufactured by Asahi Glass Co., Ltd.) to allow a hydrophilized portion to be formed to have such a thickness as shown in Table 3 and dried at 60° C. for 30 minutes, whereafter a monomer was cured by UV irradiation, thereby forming a hydrophilized portion to produce an evaluation sample (base having a hydrophilized portion).

In Comparative Example 9, the weight ratio between a hydrophilic monomer and a cross-linking agent is controlled to achieve a predetermined water contact angle.

(Method of Evaluating Antibacterial Properties)

While the evaluation on antibacterial properties was based on the evaluation method defined in JIS Z 2801:2010, the test was conducted with a contact time with a bacterial suspension of 1 hour instead of 24 hours. The number of

TABLE 2

| | Hydrophilized portion | | | | | | | Evaluation | | |
|---|---|---|---|---|---|---|---|---|---|---|
| | First antibacterial agent content (parts by weight) | Second antibacterial agent content (parts by weight) | Silver content P (ng/cm$^2$) | Silver ion amount Q (ng/cm$^2$) | P/Q | Silver content rate (wt %) | Water contact angle (°) | Antifogging properties | Initial antibacterial properties | Antibacterial properties after durability test |
| Comparative Example 4 | 0.5 | 0.5 | 70 | 12.3 | 5.7 | 0.018 | 10 | A | B | C |
| Example 6 | 1.0 | 0.5 | 130 | 15.7 | 8.3 | 0.033 | 10 | A | A | B |
| Example 7 | 1.5 | 0.5 | 190 | 18.6 | 10.2 | 0.048 | 10 | A | A | A |
| Example 8 | 2.0 | 0.5 | 250 | 21.1 | 11.8 | 0.063 | 10 | A | A | A |
| Example 9 | 2.5 | 0.5 | 310 | 23.7 | 13.1 | 0.078 | 10 | A | A | A |
| Comparative Example 5 | 1.0 | 0.05 | 121 | 24 | 5.0 | 0.030 | 10 | A | A | C |
| Example 10 | 1.0 | 0.15 | 123 | 20 | 6.2 | 0.031 | 10 | A | A | B |
| Comparative Example 6 | 0.5 | 0 | 60 | 14.1 | 4.3 | 0.015 | 10 | A | B | C |

As can be seen from Table 2, it was confirmed that the base having a hydrophilized portion of the invention has excellent antifogging properties, exhibits excellent antibacterial properties in a short time and retains excellent antibacterial properties over long periods. In particular, it was confirmed that when P/Q is 10 or more as in Examples 7 to 9, further excellent effects are exhibited.

On the other hand, in Comparative Examples 4 to 6 in which predetermined requirements are not satisfied, antifogging properties are excellent but for antibacterial properties over long periods, the desired effects are not obtained.

From above results, the effects of Embodiment 2 of the invention are apparent.

bacteria (cell/cm$^2$) after the test was measured with each sample and the evaluation was made according to the criteria below. The bacterial strain used was *Escherichia coli*. "A" or "B" is preferred in practical use. The results are shown in Table 3.
A: The number of bacteria was less than 5 cell/cm$^2$.
B: The number of bacteria was 5 cell/cm$^2$ or more but less than 10 cell/cm$^2$.
C: The number of bacteria was 10 cell/cm$^2$ or more.

(Light Resistance Test)

The color change of the hydrophilized portion in each evaluation sample having been exposed to light (UV) at an output of 60 W/m$^2$ for 10 hours in a Xenon weather meter (Suga Test Instruments Co., Ltd.) was visually evaluated in terms of the points below. "A" is preferred in practical use. The results are shown in Table 3.
A: No color change was found.
B: Color change was found.

The above-described extraction test was conducted using the evaluation sample obtained in each of Examples and Comparative Examples.

The water contact angle of the hydrophilized portion in the evaluation sample obtained in each of Examples and Comparative Examples was measured by the above-described method. The results are shown in Table 3.

In Table 3, "Antibacterial agent weight (wt %)" refers to the antibacterial agent content (wt %) with respect to the weight of a curable material ingredient (weight of total solids in the curable composition) in the hydrophilized portion.

In Table 3, each value in the "Ag ion amount" field represents the silver ion amount per unit area as measured in the extraction test.

(2) Evaluation on Antifogging Properties

In the incubator 10, the resultant hydrophilized portion-forming curable composition was applied on the inner surface of the front surface part, i.e., the front part 14a and the inclined part 14b of the incubator hood 14 and cured (by UV irradiation) to thereby provide an antibacterial agent-containing, antibacterial-treated hydrophilized portion. The hydrophilized portion had an average thickness of about 2 µm.

The water contact angle of the hydrophilized portion on the incubator hood of the incubator obtained in each of Examples and Comparative Examples was measured by the above-described method.

The method of evaluating antifogging properties is the same as the evaluation method used for Examples 11 to 15 and Comparative Examples 1 to 3 described above.

The results are all shown in Table 3.

TABLE 3

| | Hydrophilized portion | | | Evaluation | | | |
|---|---|---|---|---|---|---|---|
| | Antibacterial agent weight (wt %) | Film thickness (µm) | Ag ion amount (ng/cm$^2$) | Antibacterial properties | Light resistance | Antifogging properties | Water contact angle (°) |
| Example 11 | 0.5 | 4.0 | 15.8 | A | A | B | 25 |
| Example 12 | 0.7 | 4.0 | 19.1 | A | A | B | 20 |
| Example 13 | 1.0 | 4.0 | 23.2 | A | A | B | 22 |
| Example 14 | 1.5 | 4.0 | 25.0 | A | A | B | 23 |
| Example 15 | 2.0 | 5.0 | 40.0 | A | A | B | 25 |
| Comparative Example 7 | 0.5 | 2.0 | 6.3 | C | A | B | 23 |
| Comparative Example 8 | 3.0 | 5.0 | 63.2 | A | B | B | 21 |
| Comparative Example 9 | 1.5 | 4.0 | 20.2 | B | A | C | 50 |

As can be seen from Table 3, the base having a hydrophilized portion of the invention has excellent antifogging properties, exhibits excellent antibacterial properties in a short time and has excellent light resistance.

On the other hand, in Comparative Example 7 in which the silver ion amount is smaller than the lower limit of a predetermined range, desired antibacterial properties are not obtained and in Comparative Example 8 in which the silver ion amount is larger than the upper limit of the predetermined range, light resistance is deteriorated. In Comparative Example 9 in which the water contact angle is larger than the upper limit of the predetermined range, desired antifogging properties are not obtained and antibacterial properties are also deteriorated.

From above results, the effects of Embodiment 3 of the invention are apparent.

Examples 16 to 33 and Comparative Examples 10 to 11

Preparation of Antibacterial Agent

Synthesis Example 1

Antibacterial Agent Containing Silver Carried on Calcium Zinc Phosphate

Calcium hydroxide, zinc oxide and phosphoric acid were reacted to obtain phosphate. Silver nitrite was added to the phosphate, followed by washing, filtration, drying and fracturing, thereby obtaining an antibacterial agent A. The resultant antibacterial agent A had an average particle size of 0.9 µm and a silver ion content equivalent to 3 wt % with respect to the total weight of the antibacterial agent.

Synthesis Example 2

Antibacterial Agent Containing Silver Carried on Calcium Zinc Phosphate

Synthesis Example 1 was repeated except that fracturing was performed to allow the average particle size after fracturing to be 0.5 µm, thereby obtaining an antibacterial agent B. The resultant antibacterial agent B had a silver ion content equivalent to 1 wt % with respect to the total weight of the antibacterial agent.

Synthesis Example 3

Silver-Carrying Porous Carrier

Zeolite was brought into contact with an aqueous silver nitrite solution to substitute silver ions for ion-exchangeable ions in the zeolite, thereby obtaining a silver-carrying porous carrier A. The porous carrier A had an average particle size of 2.0 µm and a silver ion content equivalent to 0.5 wt % with respect to the total weight of the porous carrier.

EXAMPLES AND COMPARATIVE EXAMPLES

A component synthesized in any of Synthetic Examples 1 to 3 or zeolite was added and mixed into the curable composition prepared in the same manner as in Examples 6 to 10 and Comparative Examples 4 to 6 described above according to the relevant proportion (wt %) shown in Table 4, thereby preparing a hydrophilized portion-forming curable composition. The proportion (wt %) above refers to the content of each component with respect to the total weight of the hydrophilized portion formed.
<Evaluations>
(1) Evaluation on Antibacterial Properties The resultant hydrophilized portion-forming curable composition was applied to a polycarbonate sheet (Carboglass CFR110C, manufactured by Asahi Glass Co., Ltd.) and dried at 60° C. for 30 minutes, whereafter a monomer was cured by UV irradiation, thereby forming the hydrophilized portion to produce an evaluation sample (base having a hydrophilized portion). The amount of applied curable composition was adjusted to allow the hydrophilized portion to have such a thickness (hydrophilized portion average thickness) as shown in Table 4.

(Evaluation on Initial Antibacterial Properties: Evaluation on Short-Term Antibacterial Properties)

While the evaluation on antibacterial properties (initial antibacterial properties) was based on the evaluation method defined in JIS Z 2801:2010, the test was conducted with a contact time with a bacterial suspension of 1 hour instead of 24 hours. The number of bacteria (cell/cm$^2$) after the test was measured with each sample and the evaluation was made according to the criteria below. The bacterial strain used was *Escherichia coli*. In order to confirm that the test proceeds successfully, the evaluation was simultaneously made with a polycarbonate sheet (Carboglass CFR110C, manufactured by Asahi Glass Co., Ltd.) provided with no hydrophilic portion and it was confirmed that the number of bacteria (cell/cm$^2$) after 1-hour contact was 6.2×10$^2$ (cell/cm$^2$) or more. "A" or "B" is preferred in practical use.

A: The number of bacteria was less than 1 cell/cm$^2$.
B: The number of bacteria was 1 cell/cm$^2$ or more but less than 10 cell/cm$^2$.
C: The number of bacteria was 10 cell/cm$^2$ or more.

(Evaluation on Antibacterial Properties after Durability Test)

The durability test was conducted as described below for the purpose of evaluating whether each evaluation sample prepared by the foregoing procedure exhibits antibacterial properties over long periods. In general, the hydrophilized portion disposed on a surface of a member is, when gets dirty, wiped with a wet cloth in most cases and at this time, silver is dissolved and released into water. This is the main cause of impairing antibacterial properties. Therefore, if excellent antibacterial properties are exhibited even after the following abrasion test, this proves that antibacterial properties can be retained over long periods even after the use of the hydrophilized portion.

In the durability test, each evaluation sample (base having a hydrophilized portion) prepared by the foregoing procedure was rubbed 36,000 times with a compress under a load of 500 g applied to the hydrophilized portion surface and thereafter, the test for evaluating antibacterial properties was conducted by the method described above (in the paragraphs for antibacterial properties) and the evaluation was made according to the criteria below. The bacterial strain used was *Escherichia coli*. The compress used was a polyester fabric (product name: Anticon) soaked in pure water. "A" or "B" is preferred in practical use.

A: The number of bacteria was less than 1 cell/cm$^2$.
B: The number of bacteria was 1 cell/cm$^2$ or more but less than 10 cell/cm$^2$.
C: The number of bacteria was 10 cell/cm$^2$ or more.

"Zeolite" in the "Porous carrier" field in Table 4 refers to zelolite used in Synthetic Example 3 and carries no silver.

A surface of the hydrophilized portion obtained in each Example had a water contact angle of 40° or less.

The hydrophilized portion obtained in each Example had therein the porous carrier positioned to partially protrude from a surface (flat face) of the hydrophilized portion.

In Table 4, the average particle size is a value obtained by measuring the 50% volume cumulative diameter (D50) three times with a laser diffraction/scattering particle size distribution analyzer manufactured by Horiba, Ltd. and averaging the three measurements.

(2) Evaluation on Antifogging Properties

In the incubator 10, the resultant hydrophilized portion-forming curable composition was applied on the inner surface of the front surface part, i.e., the front part 14a and the inclined part 14b of the incubator hood 14 and cured (by UV irradiation) to thereby provide an antibacterial agent-containing, antibacterial-treated hydrophilized portion. The hydrophilized portion had an average thickness of about 2 μm.

The water contact angle of the hydrophilized portion on the incubator hood of the incubator obtained in each of Examples and Comparative Examples was measured by the above-described method.

The method of evaluating antifogging properties is the same as the evaluation method used for Examples 1 to 5 and Comparative Examples 1 to 3 described above.

The results are all shown in Table 4.

TABLE 4

| | Antibacterial agent | | Porous carrier | | Content with respect to total weight of hydrophilized portion | | Hydrophilized portion | | | | Evaluation | | | |
|---|---|---|---|---|---|---|---|---|---|---|---|---|---|---|
| | Type | Average particle size Da (μm) | Type | Average particle size Db (μm) | Antibacterial agent (wt %) | Porous carrier (wt %) | average thickness T (μm) | T/Da | T/Db | Db/Da | Water contact angle (°) | Antifogging properties | Intial antibacterial properties | Antibacterial properties after durability test |
| Example 16 | Antibacterial agent A | 0.9 | Porous carrier A | 2.0 | 1 | 0.5 | 3 | 3.3 | 1.5 | 2.2 | 10 | A | A | B |
| Example 17 | | | | | 1.5 | 0.5 | 3 | 3.3 | 1.5 | | 10 | A | A | A |
| Example 18 | | | | | 2 | 0.5 | 3 | 3.3 | 1.5 | | 10 | A | A | A |
| Example 19 | | | | | 2.5 | 0.5 | 3 | 3.3 | 1.5 | | 10 | A | A | A |
| Example 20 | | | | | 1.5 | 0.5 | 3 | 4.4 | 2 | | 10 | A | A | A |
| Example 21 | | | | | 1.5 | 0.5 | 3 | 6.7 | 3 | | 10 | A | A | B |
| Comparative Example 11 | | | | | 1.5 | 0.5 | 8 | 8.9 | 4 | | 10 | A | A | C |
| Comparative Example 10 | Antibacterial agent A | 0.9 | — | — | 0.5 | 0 | 3 | 3.3 | — | — | 10 | A | B | C |
| Example 22 | Antibacterial | 0.9 | Porous Carrier | 2.0 | 1.5 | 0.01 | 3 | 3.3 | 1.5 | 2.2 | 10 | A | A | A |
| Example 23 | bacterial | | | | 1.5 | 0.04 | 3 | 3.3 | 1.5 | | 10 | A | A | A |

TABLE 4-continued

| | Antibacterial agent | | Porous carrier | | Content with respect to total weight of hydrophilized portion | | Hydrophilized portion | | | | | Evaluation | | |
|---|---|---|---|---|---|---|---|---|---|---|---|---|---|---|
| | | | | | | | average | | | | | | Intial | Antibacterial properties |
| | Type | Average particle size Da (μm) | Type | Average particle size Db (μm) | Antibacterial agent (wt %) | Porous carrier (wt %) | thickness T (μm) | T/Da | T/Db | Db/Da | Water contact angle (°) | Antifogging properties | antibacterial properties | after durability test |
| Example 24 | agent A | | A | | 1.5 | 0.2 | 3 | 3.3 | 1.5 | | 10 | A | A | A |
| Example 25 | | | | | 1.5 | 0.8 | 3 | 3.3 | 1.5 | | 10 | A | B | B |
| Example 26 | | | | | 1.5 | 1 | 3 | 3.3 | 1.5 | | 10 | A | B | B |
| Example 27 | Antibacterial agent B | 0.5 | Porous Carrier | 2.0 | 1 | 0.5 | 3 | 6.0 | 1.5 | 4.0 | 10 | A | B | B |
| Example 28 | | | | | 1.5 | 0.5 | 3 | 6.0 | 1.5 | | 10 | A | B | B |
| Example 29 | | | A | | 2 | 0.5 | 3 | 6.0 | 1.5 | | 10 | A | B | B |
| Example 30 | | | | | 2.5 | 0.5 | 3 | 6.0 | 1.5 | | 10 | A | B | B |
| Example 31 | Antibacterial agent C | 0.9 | Zeolite | 2.0 | 1 | 0.5 | 3 | 3.3 | 1.5 | 2.2 | 10 | A | B | B |
| Example 32 | | | | | 1.5 | 0.5 | 3 | 3.3 | 1.5 | | 10 | A | B | B |
| Example 33 | | | | | 2 | 0.5 | 3 | 3.3 | 1.5 | | 10 | A | B | B |

As can be seen from Table 4, it was confirmed that the hydrophilized portion in the base having a hydrophilized portion of the invention has sufficient antifogging properties, exhibits antibacterial properties in a short time and retains antibacterial properties over long periods.

In particular, comparing between Examples 16 and 17, it was confirmed that an antibacterial agent content of more than 1.0 wt % leads to a more excellent evaluation result of antibacterial properties after the durability test.

In addition, comparing between Examples 20 and 21, it was confirmed that a ratio (T/Da) of 6.0 or less leads to a more excellent evaluation result of antibacterial properties after the durability test.

In addition, comparing between Examples 24 and 25, it was confirmed that a porous carrier content of 0.5 wt % or less leads to a more excellent evaluation result of antibacterial properties after the durability test.

In addition, comparing between Examples 17 and 28, it was confirmed that a ratio (Db/Da) of 3.5 or less leads to more excellent evaluation results of initial antibacterial properties and antibacterial properties after the durability test.

In addition, comparing between Examples 17 and 32, it was confirmed that when silver is carried on a porous carrier, this leads to more excellent evaluation results of initial antibacterial properties and antibacterial properties after the durability test.

On the other hand, it was confirmed that while antifogging properties are exhibited in Comparative Examples 10 and 11 in which antifogging properties fall within the predetermined range, in Comparative Examples 10 using no porous carrier or in Comparative Example 11 in which the relation expressed by formula (5) is not satisfied, desired effects are not obtained.

From above results, the effects of Embodiment 4 of the invention are apparent.

What is claimed is:

1. An incubator hood having a hydrophilized portion on at least a part of its inner surface,
    wherein the hydrophilized portion contains a hydrophilic polymer and an antibacterial agent,
    wherein a surface of the hydrophilized portion has a water contact angle of up to 30°, and
    wherein the incubator hood satisfies relations expressed by formulae (1) and (2) below when a silver content per unit area in the hydrophilized portion is represented by P and an amount of silver ions per unit area as measured by an extraction test is represented by Q, $$6.0 \leq P/Q \qquad \text{Formula (1)}$$

$$15.0 \leq Q \qquad \text{Formula (2)}$$

where a unit of P is $ng/cm^2$ and a unit of Q is $ng/cm^2$,
    the extraction test being a test for determining the amount of silver ions per unit area represented by Q by using 1/500 nutrient broth defined in JIS Z 2801:2010 as extraction liquid, controlling the extraction liquid to a temperature of 35±1° C., holding the hydrophilized portion in contact with the extraction liquid for 1 hour, measuring an amount of silver ions extracted in the extraction liquid and dividing the amount of silver ions obtained by a contact area of the hydrophilized portion with the extraction liquid,
    wherein said nutrient broth defined in JIS Z 2801:2010 comprises a beef extract, peptone and sodium chloride, dissolved in water.

2. The incubator hood according to claim 1, satisfying a relation expressed by formula (3):

$$15.0 \leq Q \leq 25.0. \qquad \text{Formula (3)}$$

3. The incubator hood according to claim 1, wherein the antibacterial agent is composed of a first antibacterial agent containing silver and a second antibacterial agent containing silver and different from the first antibacterial agent.

4. The incubator hood according to claim 3,
    wherein the first antibacterial agent contains silver and a carrier selected from a group consisting of calcium zinc phosphate and calcium phosphate, and
    wherein the second antibacterial agent contains silver and a carrier composed of zeolite.

5. An incubator, comprising:
    the incubator hood according to claim 1; and
    a base table,
    wherein the incubator hood forms inside an accommodating room by covering at least a part of the base table, and
    wherein the hydrophilized portion is provided on, of the inner surface of the incubator hood, at least a part of the inner surface corresponding to an observation portion from outside of the accommodating room.

6. The incubator according to claim 5, wherein the hydrophilized portion is provided on the inner surface of a front part and/or an upper part of the incubator hood.

7. The incubator according to claim 5, wherein the hydrophilized portion is provided on the inner surface of side parts and/or a back part of the incubator hood.

8. The incubator according to claim 5, wherein the hydrophilized portion is provided on the inner surface of an upper part of the incubator hood.

9. The incubator according to claim 5, wherein the hydrophilized portion is provided over an entire area of the inner surface of the incubator hood.

10. A hydrophilic sheet attached to at least a part of an inner surface of an incubator hood of an incubator having a base table and the incubator hood which forms inside an accommodating room by covering at least a part of the base table, comprising:
  a hydrophilized portion provided on at least a part of an outer surface of the hydrophilic sheet,
  wherein the hydrophilized portion contains a hydrophilic polymer and an antibacterial agent,
  wherein a surface of the hydrophilized portion has a water contact angle of up to 30°, and
  wherein the incubator hood satisfies relations expressed by formulae (1) and (2) below when a silver content per unit area in the hydrophilized portion is represented by P and an amount of silver ions per unit area as measured by an extraction test is represented by Q, $6.0 \leq P/Q$ \hfill Formula (1)

$15.0 \leq Q$ \hfill Formula (2)

where a unit of P is ng/cm$^2$ and a unit of Q is ng/cm$^2$,
  the extraction test being a test for determining the amount of silver ions per unit area represented by Q by using 1/500 nutrient broth defined in JIS Z 2801:2010 as extraction liquid, controlling the extraction liquid to a temperature of 35±1° C., holding the hydrophilized portion in contact with the extraction liquid for 1 hour, measuring an amount of silver ions extracted in the extraction liquid and dividing the amount of silver ions obtained by a contact area of the hydrophilized portion with the extraction liquid,
  wherein said nutrient broth defined in JIS Z 2801:2010 comprises a beef extract, peptone and sodium chloride, dissolved in water.

11. A hydrophilic antibacterial film formed on at least a part of an inner surface of an incubator hood of an incubator having a base table and the incubator hood which forms inside an accommodating room by covering at least a part of the base table, in order to form a hydrophilized portion on at least a part of the inner surface of the incubator hood,
  at least a part of the hydrophilic antibacterial film being hydrophilic,
  wherein the hydrophilized portion exhibiting hydrophilicity contains a hydrophilic polymer and an antibacterial agent,
  wherein a surface of the hydrophilized portion has a water contact angle of up to 30°, and
  wherein the incubator hood satisfies relations expressed by formulae (1) and (2) below when a silver content per unit area in the hydrophilized portion is represented by P and an amount of silver ions per unit area as measured by an extraction test is represented by Q, $6.0 \leq P/Q$ \hfill Formula (1)

$15.0 \leq Q$ \hfill Formula (2)

where a unit of P is ng/cm$^2$ and a unit of Q is ng/cm$^2$,
  the extraction test being a test for determining the amount of silver ions per unit area represented by Q by using 1/500 nutrient broth defined in JIS Z 2801:2010 as extraction liquid, controlling the extraction liquid to a temperature of 35±1° C., holding the hydrophilized portion in contact with the extraction liquid for 1 hour, measuring an amount of silver ions extracted in the extraction liquid and dividing the amount of silver ions obtained by a contact area of the hydrophilized portion with the extraction liquid,
  wherein said nutrient broth defined in JIS Z 2801:2010 comprises a beef extract, peptone and sodium chloride dissolved in water.

* * * * *